United States Patent
Halazy et al.

Patent Number: 5,641,779
Date of Patent: Jun. 24, 1997

[54] SELECTIVE LIGANDS OF 5-HT$_{1D}$-5-HT$_{1B}$ RECEPTORS DERIVED FROM INDOLEPIPERAZINE WHICH ARE USEFUL MEDICAMENTS

[75] Inventors: Serge Halazy, Lagarrigue; Michel Perez; Michael Briley, both of Castres, all of France

[73] Assignee: Pierre Fabre Medicament, Boulogne, France

[21] Appl. No.: 464,734
[22] PCT Filed: Dec. 29, 1993
[86] PCT No.: PCT/FR93/01317
§ 371 Date: Jun. 29, 1995
§ 102(e) Date: Jun. 29, 1995
[87] PCT Pub. No.: WO94/15916
PCT Pub. Date: Jul. 21, 1994

[30] Foreign Application Priority Data

Dec. 30, 1992 [FR] France .................. 92 15919

[51] Int. Cl.$^6$ .................. A61K 31/495; C07D 241/36
[52] U.S. Cl. .................. 514/253; 544/373
[58] Field of Search .................. 544/373; 514/253

[56] References Cited

U.S. PATENT DOCUMENTS 3,929,793  12/1975  Popelak et al. .................. 260/268

FOREIGN PATENT DOCUMENTS 0 457 701  5/1991  European Pat. Off. .
2 082 175  3/1982  United Kingdom .

OTHER PUBLICATIONS

M.J. Millan, S 14671: A Naphtylpiperazine 5HT Angonist, Journal of Pharmacology and Experimental Therapeutics, vol. 262 (2), pp. 451–463.

Primary Examiner—Joseph McKane
Assistant Examiner—Richard S. Myers, Jr.
Attorney, Agent, or Firm—Dressler, Rockey Milnamow & Katz, Ltd.

[57] ABSTRACT

The present invention relates to compounds having the formula:

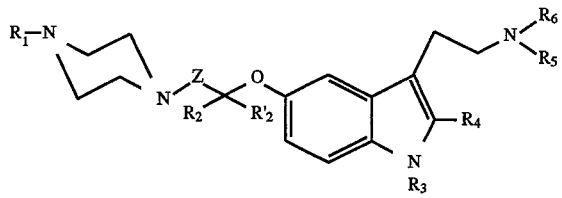

wherein $R_1$ is a hydrogen atom, a linear or branched alkyl radical or a phenyl, benzyl, cycloalkyl, polycycloalkyl, dibenzocycloalkyl, dibenzooxepine, dibenzoazepine, dibenzothiepine, benzopyrrolocycloalkyl, benzothienocycloalkyl or naphthyl radical, optionally substituted by one or a number of substituents chosen from halogen atoms and alkyl, aryl acyl, alkoxy and alkyl thio radicals.

Z is C=O, SO$_2$ or (CH$_2$)$_n$ in which n is between 1 and 5.

$R_2$ is a hydrogen atom, a linear or branched alkyl radical or a phenyl, benzyl, cycloalkyl, pyrrole, furan, pyridinyl or thiophenyl radical, optionally substituted by one or a number of substituents chosen from halogen atoms and alkyl, aryl, acyl, alkoxy and alkylthio radicals.

$R'_2$ is a hydrogen atom, a linear or branched alkyl radical or a phenyl radical.

$R_3$ is a hydrogen atom, a linear or branched alkyl radical or a benzyl or phenethyl radical.

$R_4$ is a hydrogen, chlorine, fluorine or bromine atom or a linear or branched alkyl radical.

$R_5$ is a hydrogen atom, a linear or branched alkyl radical or a benzyl or phenethyl radical.

$R_6$ is a hydrogen atom, a linear or branched alkyl radical, an acyl (COR$_7$), acyloxy (CO$_2$R$_7$) or acylamino (CONHR$_7$) radical in which R$_7$ represents a linear or branched alkyl radical, or a variously substituted phenyl radical.

19 Claims, No Drawings

SELECTIVE LIGANDS OF 5-HT$_{1D}$-5-HT$_{1B}$ RECEPTORS DERIVED FROM INDOLEPIPERAZINE WHICH ARE USEFUL MEDICAMENTS

This is a National Stage filing under 35 U.S.C. §371 of PCT/FR93/01317, filed Dec. 29, 1993, published as WO94/15916, Jul. 21, 1994.

The present invention relates to new indole compounds derived from piperazine, to processes for their preparation and to their therapeutic uses.

During the last twenty years, considerable progress has been made in understanding the biochemistry and physiology of serotonin or 5-hydroxytryptamine (5-HT), both at the level of the central nervous system and at the cardiovascular level. Thus it has been demonstrated that serotonin could play a role in certain illnesses such as depression, pain, compulsive obsessional disorders, obesity, schizophrenia, anxiety, certain sexual dysfunctionings, migraine and other vasospastic disorders. The discovery of the various subclasses of the receptors for serotonin has stimulated the search for selective ligands (cf. R. A. Glennon, Neuroscience & Biobehavioral Reviews, 14, 35–47, 1990; A. W. Schmidt and S. J. Peroutka, FASEB J., 3, 2242–2249, 1989) in order better to determine the pharmacological meaning of each of these receptor subtypes and to be able to identify new therapeutic agents which are selective, non-toxic and devoid of undesirable side effects (S. Langer, N. Brunello, G. Racagni and J. Mendlewicz, "Serotonin receptor subtypes: pharmacological significance and clinical implications", edited by Karger (1992); B. E. Leonard, Int. Clin. Psychopharmacology, 7, 13–21 (1992); D. G. Grahame-Smith, Int. Clin. Psychopharmacology, 6, suppl. 4, 6–13 (1992)).

The compounds according to the present invention are powerful and selective ligands of receptors for 5-hydroxytryptamine and more particularly of the receptor recently described as 5-HT$_{1B}$ and/or 5-HT$_{1D}$ receptor. The medicaments according to the present invention find their use in both the curative and preventive treatment of disorders related to serotonin.

Patent Application FR 2,671,971 describes a class of 5-O-carboxymethylated derivatives of tryptamine which possess good affinity for 5-HT$_{1D}$ receptors and can consequently act as therapeutic agents in the treatment of migraine. Nevertheless, Application FR 2,671,971 does formula:

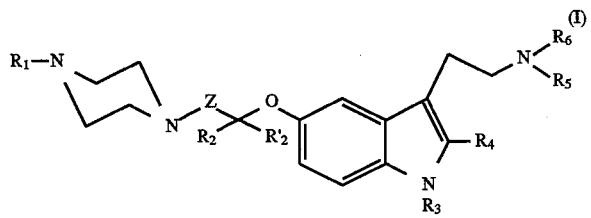

to their preparation and to the medicaments containing them.

In the formula (I):

R$_1$ represents a hydrogen atom, a linear or branched alkyl radical or a phenyl, benzyl, cycloalkyl, polycycloalkyl, dibenzocycloalkyl, dibenzooxepine, dibenzoazepine, dibenzothiepine, benzopyrrolocycloalkyl, benzothienocycloalkyl or naphthyl radical, optionally substituted by one or a number of substituents chosen from halogen atoms and alkyl, aryl, acyl, alkoxy and alkyl thio radicals.

Z represents C=O, SO$_2$ or (CH$_2$)$_n$ in which n is between 1 and 5.

R$'_2$ represents a hydrogen atom, a linear or branched alkyl radical or a phenyl, benzyl, cycloalkyl, pyrrole, furan, pyridinyl or thiophenyl radical, optionally substituted by one or a number of substituents chosen from halogen atoms and alkyl, aryl, acyl, alkoxy and alkylthio radicals.

R'$_2$ represents a hydrogen atom, a linear or branched alkyl radical or a phenyl radical.

R$_3$ represents a hydrogen atom, a linear or branched alkyl radical or a benzyl or phenethyl radical.

R$_4$ represents a hydrogen, chlorine, fluorine or bromine atom or a linear or branched alkyl radical.

R$_5$ represents a hydrogen atom, a linear or branched alkyl radical or a benzyl or phenethyl radical.

R$_6$ represents a hydrogen atom, a linear or branched alkyl radical, an acyl (COR$_7$), acyloxy (CO$_2$R$_7$) or acylamino (CONHR$_7$) radical in which R$_7$ represents a linear or branched alkyl radical, or a variously substituted phenyl radical.

In the preceding definitions and those which will be mentioned below, except when otherwise stated, the alkyl, alkoxy or alkylthio radicals contain 1 to 6 straight-or branched-chain carbon atoms, the cycloalkyl portions contain 3 to 7 carbon atoms and the polycycloalkyl portions contain 7 to 12 carbon atoms. In the formula (I), the halogen atoms are preferentially chlorine, fluorine and bromine atoms.

The compounds of formula (I) containing 1 or a number of asymmetric centers have isomeric forms. The racemates and the pure enantiomers of these compounds also form part of this invention.

The invention also comprises the salts, solvates (for example hydrates) and bioprecursors of these compounds which are acceptable in therapeutic use.

Mention will be made, among the salts of the indoles of general formula (I) which are acceptable in therapeutic use, of the salts formed by addition with organic or inorganic acids and for example hydrochlorides, hydrobromides, sulfates, fumarates and maleates. Other salts can be useful in the preparation of the compounds of formula (I), for example the adducts with creatinine sulfate.

The expression "bioprecursors" as used in the present invention applies to compounds whose structure differs from that of the compounds of formula (I), but which, administered to an animal or to a human being, are converted in the body to a compound of formula (I).

A valued class of compounds according to the invention consists of those which correspond to the general formula (Ia)

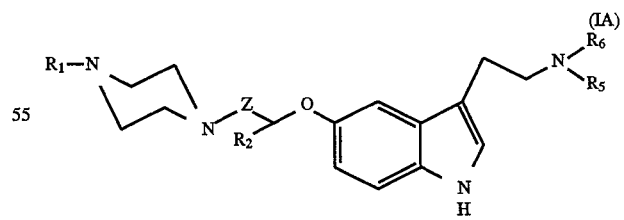

in which R$_1$, R$_2$, R$_5$ and R$_6$ are defined as above in the formula (I) and their salts, solvates (for example hydrates) and bioprecursors which are acceptable in therapeutic use.

The invention also comprises the preparation by the general processes described hereinbelow of the compounds of general formula (I) and of their salts, solvates (for example hydrates) or bioprecursors which are acceptable in therapeutic use.

According to a first general process (A), a compound of general formula (I) can be prepared by reacting a compound of general formula (II):

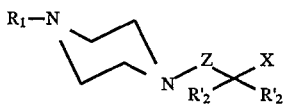

in which $R_1$, Z, $R_2$ and $R'_2$ are defined as in the formula (I) and X is defined as a leaving group such as a halogen (preferably a bromine, iodine or chlorine atom), a mesylate, a tosylate or a triflate, with a serotonin derivative of general formula (III):

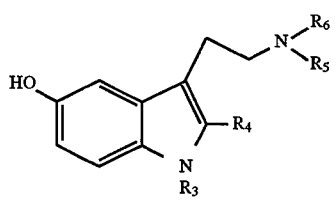

in which the $R_3$, $R_4$, $R_5$ and $R_6$ residues are defined as described above in the formula (I), apart from the fact that $R_6$ cannot be a hydrogen. The preparation of the derivatives of formula (I) in which $R_6$ is a hydrogen is carried out by hydrolysis of a derivative of formula (I) in which $R_6$ is a COR or $CO_2R_7$ group, preferably a $CO_2R_7$ group in which $R_7$ is preferentially a t-butyl or benzyl residue. The conversion of the compounds of formula (I) in which $R_6$ is a $CO_2^tBu$ (BOC) group to compounds of formula (I) in which $R_6$ is a hydrogen is preferentially carried out using an acid (such as hydrochloric acid or trifluoroacetic acid) in an organic solvent, such as ether, tetrahydrofuran, toluene, dichloromethane or chloroform, at a temperature of between $-15°$ C. and $40°$ C.

The conversion of the compounds of formula (I) in which $R_6$ is a $CO_2CH_2C_6H_5$ group (commonly known as a Z group) to compounds of formula (I) in which $R_6$ is a hydrogen is preferentially carried out by catalytic hydrogenation by preferentially using palladium-on-charcoal as catalyst, under hydrogen at atmospheric pressure, in a solvent such as THF, ethanol or isopropanol which can contain up to 10% of acetic or citric acid, at a temperature of between $0°$ and $40°$ C.

The preparation of the derivatives of formula (I) by condensation of the derivatives of formula (II) with the derivatives of formula (III) can generally be carried out in the presence of an organic base (NaH, KH, $Et_3N$, DBU, DBN, TMP, DIPEA or $^tBuOK$) or an inorganic base ($K_2CO_3$, $KHCO_3$, $NaHCO_3$, $Cs_2CO_3$, KOH, NaOH, $CaCO_3$ and the like) in an anhydrous solvent, such as THF, DMF, DMSO, acetone, diethyl ketone, methyl ethyl ketone, acetonitrile or DME, at a temperature of between $20°$ and $140°$ C., in the presence or in the absence of a salt as catalyst and which can be KI, $Bu_4NI$, LiI, $AgBF_4$, $AgClO_4$, $Ag_2CO_3$, KF, $Bu_4NF$ or CsF. The choice of the experimental conditions for carrying out the condensation between the derivatives of formula (II) and (III) in order to obtain the derivatives of formula (I) is very clearly dependent on the nature of the substituents in the reactants (II) and (III) and more particularly on the nature of the Z, $R_2$ and $R'_2$ groups. Byway of example, when Z is a carbonyl (CO) functional group, $R_2$ is a hydrogen atom and X a halogen, the condensation between (II) and (III) in order to give (I) is preferentially carried out at $80°$ C., in methyl ethyl ketone, in the presence of an excess of $K_2CO_3$ and of a catalytic amount of KI. When Z is a carbonyl group and when $R_2$ and $R'_2$ are both other than a hydrogen, the preferred method consists in reacting a derivative of formula (III) with this derivative of formula (II) in the presence of a silver salt such as silver tetrafluoroborate and of an inorganic base such as $K_2CO_3$. When the Z group is defined as $(CH_2)_n$, the condensation between the (II) and (III) derivatives is carried out in a solvent such as DMF or DMSO, in the presence of a base such as DBU or DIPEA, at $100°$ C. in the presence of a catalytic amount of KI or of $Bu_4NI$. An alternative and particularly valued method consists in condensing the (II) and (III) derivatives, under neutral conditions, in DMF, in the presence of a large excess of a fluoride such as KF, CsF or $Bu_4NF$.

The compounds of general formula (II) in which the substituents $R_1$, $R_2$, $R'_2$ and X are defined as above are prepared by methods which differ according to the nature of the Z residue. Thus the derivatives of formula (II) in which Z is a carbonyl group forming part of an amide functional group are obtained by reaction of piperazine derivatives of general formula (IV)

in which the $R_1$ residue is defined as in the formula (I), with a derivative of formula (V)

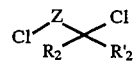

in which $R_2$ and $R'_2$ are defined as in the formula (I) and Z represents $C=O$. This reaction, which makes it possible to prepare the derivatives of formula (II) in which $Z=CO$ and $X=Cl$ from the piperazine derivatives (IV) and the acid chlorides (V), is a well-known reaction for amide formation from an amine and an acid chloride and can be carried out in a solvent such as dichloromethane, THF, chloroform, acetone, methyl ethyl ketone, DME or acetonitrile, at a temperature of between $-20°$ C. and $80°$ C., in the presence of a base such as a tertiary amine (DBU, $Et_3N$ or DIPEA) or inorganic bases such as carbonates ($KHCO_3$, $NaHCO_3$, $K_2CO_2$, $Na_2CO_3$, $CaCO_3$ or $Cs_2CO_3$), sodium hydroxide or alternatively potassium hydroxide.

The derivatives of formula (II) in which Z represents a $—(CH_2)_n—$group are generally prepared by condensation of a piperazine derivative of formula (IV) with a derivative of formula (VI)

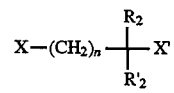

in which X represents a leaving group such as a chlorine, a bromine, an iodine or a mesylate, tosylate or triflate group, $R_2$ and $R'_2$ are defined as in the formula (I) and X' can either be identical to X or represents a group OR' in which R' is defined as a protective group for an alcohol, such as a silyl ether ($SiMe_3$, $Si^tBuMe_2$ or $SiC_6H_5Me_2$), a tetrahydropyran or alternatively a benzyl or a trityl. It is clearly understood that, in the case where X' is different from X, the condensation between the piperazine derivative (IV) and the intermediate (VI) is followed by hydrolysis of the OR' protective group in order to give an intermediate alcohol derivative which is converted to a leaving Group which leads to the compounds (II) in which $R_1$, $R_2$, $R'_2$ and X are defined as above. In the procedure mentioned above, hydrolysis of the OR' functional group to an alcohol is carried out by described methods which are appropriate according to the nature of R' (refer to the work by T. W. Greene, "Protective groups in organic synthesis", John Wiley & Sons, 1981) and the conversion of the alcohol thus obtained to a leaving Group (so as to obtain the compounds (II)) is carried out by techniques and methods which are well known for this type of conversion, such as the use of $SOCl_2$ or $POCl_3$ in dichloromethane for the formation of derivatives of formula (II) in which X=Cl, the use of $PBr_3$ or $Br_2PO_3$ for the formation of derivatives of formula (II) in which X=Br, the use of $PI_3$ or $PI_2$ or $P_2I_4$ for the forma- tion of derivatives of formula (II) in which X=I, the use of tosyl chloride for the formation of derivatives of formula (II) in which X=Tos, the use of mesyl chloride for the formation of derivatives of formula (II) in which X=Mes and finally the use of triflic anhydride for the formation of derivatives of formula (II) in which X=Tf. In the specific case of the compound (II) in which Z=$CH_2$ and $R_2$ and $R'_2$ are hydrogens, a preferred method of preparation consists in treating the piperazine of formula (IV) with ethylene oxide in the presence of a base, such as a tertiary amine, $^tBuOK$, LiH, NaH, sodium hydroxide, $K_2CO_3$ or $Li_2CO_3$, in order to lead to the derivative of formula (II) in which Z=$CH_2$ and $R_2$ and $R'_2$ hydrogens, after conversion of the intermediate alcohol to a leaving Group X defined in the formula (II), after conversion as described above.

The derivatives of formula (II) in which Z=$SO_2$ are Generally prepared by reaction of the piperazine derivatives of general formula (IV), in which the $R_1$ group is defined as in the general formula (I), with a derivative of formula (V) in which $R_2$ and $R'_2$ are defined as in the formula (I) and Z represents $SO_2$.

The compounds of general formula (I) can also be prepared according to a second general process (B), by reacting a compound of general formula (IV):

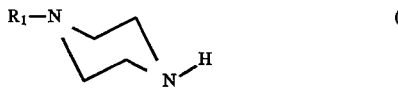
(IV)

in which $R_1$ is defined as in the general formula (I), with a serotonin derivative of general formula (VII)

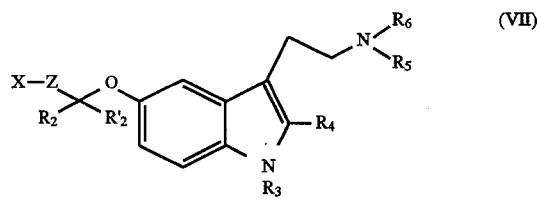
(VII)

in which the $R_2$, $R'_2$, $R_3$, $R_4$, $R_5$ and $R_6$ residues are defined as described above in the formula, apart from the fact that $R_6$ cannot be a hydrogen, and X is defined as a leaving group such as a halogen (preferably a bromine, iodine or chlorine atom), a mesylate, a tosylate or a triflate or the precursor of a leaving group such as a hydroxyl radical.

The preparation of the derivatives of formula (I) in which $R_6$ is a hydrogen by the general process (B) (condensation of the intermediates (IV) and (VII)) is carried out by hydrolysis of a derivative of formula (I) in which $R_6$ is an amine-protective group as described above.

The preparation of the derivatives of formula (I) by condensation of the intermediates of formula (IV) with the derivatives of formula (VII) is carried out by using methods which are related to the nature of the Z substituent. Thus the preparation of the compounds of formula (I) in which Z is a carbonyl (CO) residue by the general process (B) is carried out by condensation of the piperazine derivative (IV) with a carboxylic acid derivative (VII) (X=OH, Z=CO) by techniques and methods which are well known in peptide synthesis. Thus the carboxylic acid (VII) (X=OH, Z=CO) can be converted beforehand to the acid chloride (X=Cl, Z=CO) by reaction with thionyl chloride, oxalyl chloride or phosphorus oxychloride, in an inert solvent such as dichloromethane or chloroform, acetonitrile or THF, at a temperature of between −25° C. and +25° C., in the presence of an amine base such as triethylamine, DIPEA or N-methylmorpholine. The condensation between this acid chloride thus obtained and the piperazine derivative (IV) is then carried out in the same solvent, at a temperature of between 0 and 50° C., in order to give the products of formula (I) in which Z represents CO. A valued method for preparing the derivatives of formula (I) in which Z represents CO by the general process (B) consists in treating a carboxylic acid derivative of formula (VII) in which X=OH and Z=CO with ethyl chloroformate in a solvent such as dichloromethane, dichloroethane, chloroform or acetonitrile, in the presence of a tertiary amine such as triethylamine, diisopropylethylamine or N-methylmorpholine, at a temperature of between −20° C. and 0° C.; the piperazine derivative is then added to the reaction mixture, which is stirred at a temperature of between 0° and 35° C. for a time ranging from 2 to 8 hours.

A preferred method for preparing the derivatives of formula (I) in which Z represents CO by the general process (B) consists in treating 1-methyl-2-chloropyridinium iodide with a mixture containing a carboxylic acid of formula (VII) (in which X=OH and Z=CO), a piperazine derivative of formula (IV) and a tertiary amine such as tributylamine in an inert anhydrous solvent such as dichloromethane, chloroform or acetonitrile at a temperature of between 30° C. and 80° C.

The preparation of the derivatives of formula (I) in which Z represents a —$(CH_2)_n$— residue by the general process (B) is carried out by condensation between a piperazine derivative of formula (IV) in which $R_1$ is defined as above and an intermediate of general formula (VII) in which X is a leaving group such as a halogen (preferentially a bromine, chlorine or iodine atom), a mesylate, a tosylate or a triflate, Z represents —$(CH_2)$—$_n$, and $R_2$, $R'_2$, $R_3$, $R_4$, $R_5$ and $R_6$ are defined as in the formula (I). This reaction can be carried out in the presence of an organic base (NaH, $^tBuOK$, DBU or DIPEA) or an 5 inorganic base (KOH, $K_2CO_3$, $NaHCO_3$ or $Cs_2CO_3$) in an anhydrous solvent such as THF, DMF, DMSO, acetonitrile or methyl ethyl ketone at a temperature of between 20 and 100° C.

The intermediates of formula (VII) can be prepared by condensation of a serotonin derivative of formula (VIII)

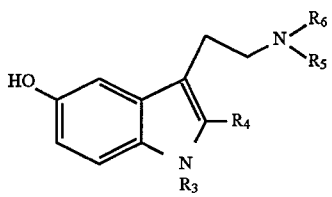

(VIII)

in which $R_3$, $R_4$, $R_5$ and $R_6$ are defined as in the formula (I), apart from the fact that $R_6$ must be other than a hydrogen, with a derivative of formula (IX)

(IX)

in which X" is a group OR where R is a conventional protective group such as $CH_3$, $C_2H_5$, $CH_2C_6H_5$ or $^tC_4H_9$ when Z represents $SO_2$ or CO (it then concerns esters in which X"-Z represent ROCO or $ROSO_2$) and a silyl (trimethylsily triethylsilyl or t-butyldimethylsilyl), benzyl, tetrahydropyranyl or trityl group in the case where Z represents —$(CH_2)_n$—and X' represents a leaving group such as a halogen (preferably a chlorine, an iodine or a bromine), a mesylate, a tosylate or a triflate. This condensation reaction between the intermediates (VIII) and (IX) as described above is carried out in basic medium (in the presence of a base such as NaH, KH, $^tBuOK$, $K_2CO_3Cs_2CO_3$, DIPEA or DBU) in an anhydrous solvent such as DMSO, DMF, THF, acetonitrile, methyl ethyl ketone or DME at a temperature of between 0° C. and 100° C., according to the nature of Z. In the specific case where Z represents CO and where $R_2$, $R'_2$, $R_3$, $R_4$ and $R_5$ represent a hydrogen and $R_6$ a t-butoxycarbonyl residue, this reaction has been described in Patent Application FR 2,671,971.

In the specific case of the derivatives of formula (I) in which $R_1$, $R_3$, $R_4$ and $R_5$ are described as above but where Z represents —$(CH_2)_n$— and $R_6$ is other than COR, a preferred method of synthesis consists in reducing the corresponding derivatives of formula (I) in which Z represents CO by a reducing agent which makes it possible to convert an amide to an amine, such as borane ($BH_3$. $Me_3S$) or $LiAlH_4$, the methods and techniques which are well known for this type of reduction being used.

In the specific case of compounds of formula (I) in which $R_1$, $R_3$, $R_4$, $R_5$ and $R_6$ are described as above, Z represents $SO_2$ and $R_2$ and $R'_2$ are hydrogen atoms, the most particularly valued method of preparation according to the procedure (B) consists in condensing a serotonin derivative of structure (VIII), in which $R_3$, $R_4$ and $R_5$ are described as above and $R_6$ is other than a hydrogen, with an intermediate of formula (IX), in which X" represents OH, Z represents $SO_2$, $R_2$ and $R'_2$ represent a hydrogen and X' represents a chlorine, according to the method described by H. J. Barber et al. [J. Appl. Chem. (London), 3, 253 (1953)]. The products (VII) thus obtained in which X" represents OH, $R_2$ and $R'_2$ represent a hydrogen and Z represents $SO_2$ are converted to intermediates (VII) in which X represents a chlorine or a bromine and condensed, as described above, with a piperazine of structure (IV) in order to give the product of formula (I).

The possibility of converting derivatives of formula (I) initially prepared by the processes (A) and (B) described above to new derivatives of formula (I) by techniques and methods which are well known to a person skilled in the art should also be regarded as part of this invention. Thus, and by way of example, the derivatives of formula (I) in which $R_3$ represents a hydrogen can be elaborated to derivatives of formula (I) in which $R_3$ represents an alkyl, benzyl or acyl residue by reaction respectively with an alkyl halide, a benzyl halide or an acid chloride or acid anhydride, in basic medium, by methods and techniques which are well known in this type of reaction and which, by way of example, are described in "The Chemistry of Indoles", edited by R. S. Sundberg, Volume 18 of "Organic Chemistry, A Series of Monograph", Academic Press, New York, 1970.

It will be understood that, in some of the above conversions, it may be necessary or desirable to protect possible sensitive groups of the molecule in question in order to avoid undesirable side reactions. This can be carried out by the use of conventional protective groups such as those described in "Protective Groups in Organic Synthesis", edited by J. F. McOwie, Plenum Press, 1973 and in T. W. Greene, Protective Groups in Organic Synthesis, John Wiley & Sons, 1981. The protective groups can be removed during any appropriate subsequent stage, by using methods and techniques which are also described in the abovementioned references. Thus in certain specific cases, it may be necessary to protect the indole nitrogen during the preparation of compounds of formula (I) in which $R_3$ represents a hydrogen.

When it is desired to isolate a compound according to the invention in the form of a salt, for example in the form of a salt formed by addition with an acid, it is possible to achieve this by treating the free base of general formula (I) with an appropriate acid, preferably in an equivalent amount, or with creatinine sulfate in an appropriate solvent.

When the processes described above for preparing the compounds of the invention give mixtures of stereoisomers, these isomers can be separated by conventional methods such as preparative chromatography.

When the new compounds of general formula (I) have one or a number of asymmetric centers, they can be prepared in the form of a racemic mixture or in the form of enantiomers, whether this is by enantioselective synthesis or by resolution. The compounds of formula (I) having at least one asymmetric center can, for example, be separated into their enantiomers by the usual techniques such as the formation of diastereomeric pairs by formation of a salt with an optically active acid such as (−)-di-p-toluoyl-l-tartaric acid, (+)-di-p-toluoyl-1-tartaric acid, (+)-camphorsulfonic acid, (−)-camphor-sulfonic acid, (+)-phenylpropionic acid or (−)-phenyl-propionic acid, followed by fractional crystallization and regeneration of the free base. The compounds of formula (I) in which $R_6$ is a hydrogen comprising at least one asymmetric center can also be resolved by formation of diastereomeric aides which are separated by chromatography and hydrolysed in order to release the chiral auxiliary.

Generally, the compounds of formula (I) can be purified by the usual methods, for example by crystallization (in particular when the compounds of formula (I) are isolated in the salt form), chromatography or extraction.

The examples which follow illustrate the invention without, however, limiting the scope thereof.

EXAMPLE 1

4-o-Tolyl-1-.(tryptamine-5-O-carboxymethyl)-piperazide hydrochloride

Method B

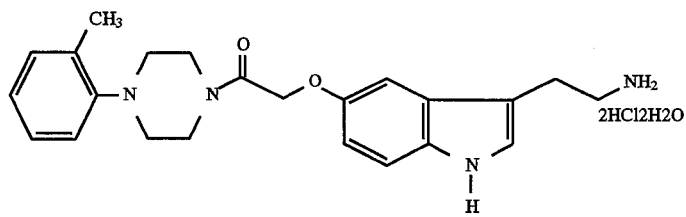

2HCl2H2O

1A—tert-Butoxycarbamate of 5-hydroxytryptamine:

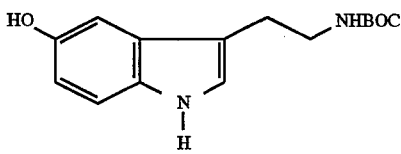

1A

The creatine sulfate monohydrate salt of serotonin (20 g, 49.3mmol) is treated with di-tert-butyl dicarbonate (16.1 g, 74 mmol) in water (360 ml) in the presence of 2N sodium hydroxide (72 ml) at room temperature. After 1 hour, the reaction mixture is diluted with ethyl acetate (600 ml) and stirred for 10 minutes. The 2 phases formed are separated by settling; the organic phase is washed with water, dried over sodium sulfate, filtered and then evaporated to dryness. The syrup obtained is chromatographed on a column of silica gel eluted with a dichloromethane/methanol (20:1; v/v) mixture. The pure compound is isolated in the form of a brown syrup (11.1 g; 81%).

Elemental analysis ($C_{15}H_{20}N_2$, $O_3$), % calculated: C 65.20; H 7.30; N 10.14; % found: C 64.15; H 7.47; N 9.77.

Proton nuclear magnetic resonance spectrum, $CDCl_3$ (ppm): 1.44 s, 9H (tBu); 2.86 t, 2H ($CH_2$); 3.45 m, 2H ($CH_2$); 4.68 s, 1H (NH); 5.59 s, 1H (O-H); 6.77–7.26 m, 4H (Ar); 7.99 s, 1H (NH).

1B—tert -Butoxycarbamate of tryptamine- 5 - (methyl -0-acetate):

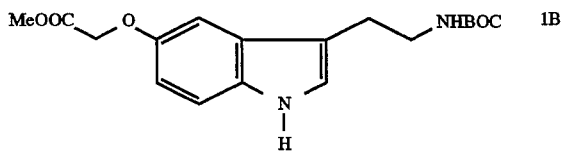

1B

The compound 1A (5.5 g; 20.07 mmol) in solution in methyl ethyl ketone (70 ml) in the presence of potassium carbonate (6.9 g; 50.1mmol) and of potassium iodide (33 mg; 0.2 mmol) is treated dropwise with methyl bromoacetate (3.3 ml; 36.1 mmol). The mixture is then brought to reflux for 5 hours, returned to room temperature, filtered on celite and evaporated to dryness. The syrup is taken up in ethyl ether and washed with 0.5N sodium hydroxide and then with water. The organic phase is dried over sodium sulfate, filtered and then evaporated to dryness. The yellow solid obtained is chromatographed on a column of silica gel eluted with a chloroform/methanol/ aqueous ammonia (95:4.5:0.5; v/v) mixture. The pure compound is isolated (6.4 g; 91%).

Elemental analysis ($C_{18}H_{24}N_2O_5$), % calculated C 62.06; H 6.94; N 8.04; % found: C 61.44; H 6.88; N 7.52.

Proton nuclear magnetic resonance spectrum, $CDCl_3$ (ppm): 1.44 s, 9H (tBu); 2.88 t, 2H ($CH_2$); 3.42 m, 2H ($CH_2$); 3.82 s, 3H (OMe); 4.77 s, 3H ($COCH_2O$+NH); 6.88–7.28 m, 4H (Ar); 8.38 s, 1H (NH).

1C—tert-Butoxycarbamate of tryptamine-5-(0-acetic acid):

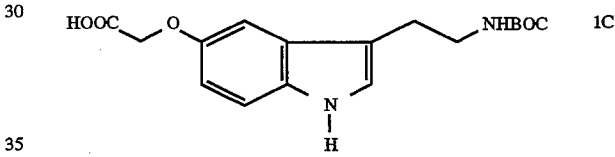

1C

The compound 1B (14.0 g; 40.24 mmol) in solution in ethanol (250 ml) and water (1 ml) is treated with potassium hydroxide pellets (8.9 g; 157 mmol) at room temperature for 3 hours. The mixture is then concentrated by evaporation, diluted with water, acidified with hydrochloric acid (1N) to pH 3 and extracted with ethyl acetate. The organic phase is dried over sodium sulfate, filtered and then evaporated to dryness.

The yellow syrup obtained (12.1 g; 90 %) is used without other purification.

Proton nuclear magnetic resonance spectrum, $CDCl_3$ (ppm): 1.44 s, 9H (tBu); 2.88 t, 2H ($CH_2$); 3.42 m, 2H ($CH_2$); 4.70 s, 2H ($COCH_2O$); 4.98 s, 1H (NH); 6.90–7.30 m, 4H (Ar); 8.05 s, 1H (NH).

1D—4-o-Tolyl-1- (tert-butoxycarbamate-tryptamine-5-O-carboxymethyl) piperazide hydrochloride:

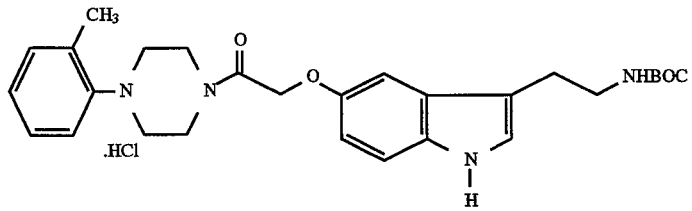

1D

A mixture of the compound 1C (1.0 g; 2.99 mmol) and of N-methylmorpholine (0,362 ml; 3.3 mmol) in dichloromethane at −10° C. is treated dropwise with ethyl chloroformate. After stirring for 10 minutes, orthotolylpiperazine (1.1 g; 4.5 mmol) is added and the mixture is then stirred for 2 hours from −10° C. to room temperature. The mixture is then diluted with dichloromethane and washed with sodium bicarbonate and then with water. The organic phase is dried over sodium sulfate, filtered and evaporated. The syrup obtained is chromatographed on a column of silica gel eluted with a dichloromethane/methanol (20:1; v/v) mixture. The pure compound is isolated in the form of a white solid (1.16g; 69 %) recrystallized from ethyl ether. The compound obtained is diluted in dichloromethane and the hydrochloride is formed by addition of the necessary amount of hydrochloric acid in ether. The crystals are recrystallized from ethyl acetate.

Elemental analysis ($C_{28}H_{37}N_4O_4Cl$); % calculated: C 63.56; H 7.04; N 10.59; % found: C 64.31; H 6.88; N 10.65.

Proton nuclear magnetic resonance spectrum, $d_6$-DMSO (ppm): 1.38 s, 9H (tBu); 2.28 s, 3H ($CH_3$); 2.79 m, 6H ($CH_2$); 3.21 m, 2H ($CH_2$); 3.65 s, 2H ($CH_2$); 4.80 s, 2H ($COCH_2O$); 6.75–7.26 m, 8H (Ar), 10.67 s, 1H (NH).

Melting point: 134° C.

1 - 4-o-Tolyl-1-(tryptamine-5-O-carboxymethyl)piperazide hydrochloride:

The compound 1D in the form of the free base (200 mg; 0.41 mmol) in solution in toluene (10 ml) is treated with trifluoroacetic acid (2 ml). After stirring for 1 hour at room temperature, the mixture is diluted with ethyl acetate and washed with 2N sodium hydroxide (twice), with water and then with a saturated sodium chloride solution. The organic phase is dried over sodium sulfate, filtered and evaporated.

The syrup obtained is chromatographed on a column of silica gel eluted with a chloroform/methanol/aqueous ammonia (85:14:1, v/v) mixture. The pure product is isolated in the form of a colorless syrup (92 mg; 57%). The compound obtained is diluted in dichloromethane and the hydrochloride is formed by addition of the necessary amount of hydrochloric acid in ether.

Elemental analysis ($C_{23}H_{34}N_4O_4Cl_2$), % calculated: C 61.53; H 6.08; N 10.25; % found: C 61.25; H 6.07; N 10.06.

Proton nuclear magnetic resonance spectrum, $d_6$-DMSO (ppm): 2.30 s, 3H ($CH_3$); 2.85–3.00 m, 8H ($CH_2$); 3.66 s, 4H ($CH_2$); 4.85 s, 2H ($COCH_2$); 6.76–7.29 m, 8H (Ar); 8.05 s, 3H ($NH_3^+$); 10.86 s, 1H ($NH^+$).

Melting point: 147° C.

EXAMPLE 2

4-o-Tolyl-1-(tryptamine-5-O-carboxymethyl) piperazide hydrochloride

Method A

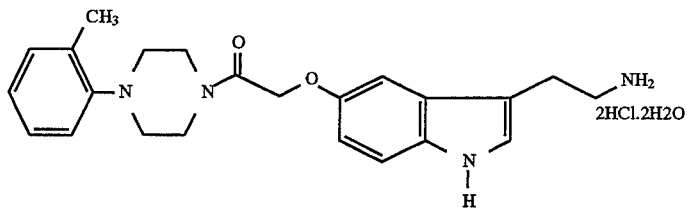

2

2A—4-o-Tolyl-1-chloroacetyl-piperazide:

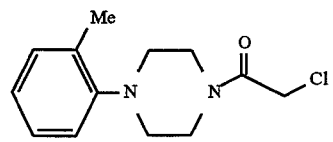

2A ortho-Tolylpiperazine (3.5 g; 20.0 mmol) in solution in methyl ethyl ketone (35 ml), in the presence of calcium carbonate (6 g; 60.0 mmol), is treated dropwise at 0° C. with chloroacetyl chloride (1.59 ml; 20.0 mmol). After 15 minutes, the mixture is diluted with ethyl acetate, filtered on celite and washed with water and then with a sodium chloride solution. The organic phase is dried over sodium sulfate, filtered and evaporated. The yellow solid obtained (3.7 g; 74%) is used without other purification in the following stage.

2B—4 -o-Tolyl-1-(tert -butoxycarbamate- tryptamine-5-O-carboxymethyl) piperazide hydrochloride:

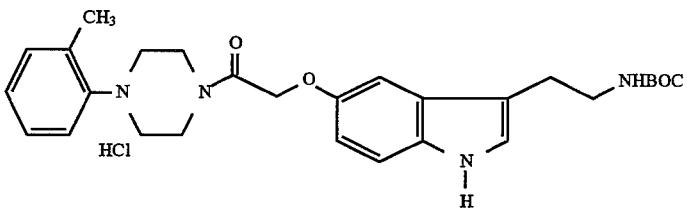

2B

A mixture of the compound 1A (2.27 g; 8.23 mmol) and of the compound 2A (3.7 g; 14.8 mmol) in methyl ethyl ketone (45 ml), in the presence of potassium carbonate (2.8 g; 20.6 mmol) and of potassium iodide (70 mg; 0.41 mmol), is heated at reflux for 5 hours. The mixture is then diluted with ethyl acetate, filtered on celite and washed with sodium hydroxide solution (0.5N), with water and then with a saturated sodium chloride solution. The organic phase is dried over sodium sulfate, filtered and then evaporated to dryness. The syrup obtained is chromatographed on a column of silica gel eluted with a dichloromethane/ethyl acetate (4:1; v/v) mixture. The pure product is isolated in the form of a colorless syrup (3.16 g; 78% for the 2 stages).

This product is diluted in dichloromethane and the hydrochloride is formed by addition of the necessary amount of hydrochloric acid in ether. The crystals are recrystallized from ethyl acetate.

The structural and physical characteristics are described in Example 1D.

2-4-o-Tolyl-1-(tryptamine-5-O-carboxymethyl)piperazide hydrochloride:

The product 2B (3.2 g; 6.61 mmol) leads to the product 2 (1.7 g; 67%) by the method described beforehand for the synthesis of the product 1 from 1D. The product 2 obtained has the same structural and physical characteristics as Example 1.

EXAMPLE 3

4-(a,a,a-Trifluoro-m-tolyl)-1-(tryptamine-5-O-carboxymethyl) piperazide hydrochloride

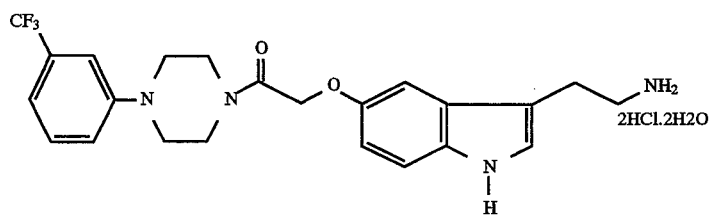

3

2HCl.2H2O

The compound 3 is obtained from 1-(a,a,a-trifluoro-m-tolyl)piperazine (0.338 ml; 1.8 mmol), chloroacetyl chloride (0.143 ml; 1.8mmol) and the tert-butoxycarbamate of 5-hydroxytryptamine 1A (276 mg; 1.0 mmol) according to the procedure described in the preparation of Example 2. The purification of the product in the base form is carried out by chromatography on a column of silica gel eluted with a chloroform/methanol/aqueous ammonia (85:14:1; v/v) mixture. The pure product is isolated in the form of a colorless syrup which leads, after treatment with hydrochloric acid in ether, to the dihydrochloride dihydrate of the compound 3 (258 mg; 58%).

Elemental analysis ($C_{23}H_{31}Cl_2F_3N_4O_4$), % calculated: C 49.73; H 5.62; N 10.08; % found: C 49.73; H 5.12; N 9.94.

Proton nuclear magnetic resonance spectrum, $d_6$-DMSO (ppm): 2.99 m, 4H ($CH_2$); 3.30 m, 4H ($CH_2$); 3.67 m, 4H ($CH_2$); 4.83 s, 2H ($COCH_2O$); 6.77–7.49 m, 8H (Ar); 8.01 s, 3H ($NH_3^+$); 10.86 s, 1H (NH).

Melting point: 131° C.

EXAMPLE 4

4-(Naphth-1-yl)-1-(tryptamine-5-O-carboxymethyl) piperazide hydrochloride

The compound 4 is obtained from 1-naphthylpiperazine (478 mg; 2.25 mmol), chloroacetyl chloride (0,179 ml; 2.25 mmol) and the tert-butoxycarbamate of 5-hydroxytryptamine 1A (341 rag; 1.24 retool) according to the procedure described in the preparation of Example 2. The purification of the product in the base form is carried out by chromatography on a column of silica gel eluted with a chloroform/methanol/aqueous ammonia (80:19:1; v/v) mixture. The pure product is isolated in the form of a colorless syrup which leads, after treatment with hydrochloric acid in ether, to the compound 4.

Elemental analysis ($C_{26}H_{30}Cl_2N_4O_2$. $1/3Et_2O$), % calculated: C 62.34; H 6.39; N 10.65; % found: C 62.52; H 6.49; N 10.45.

Proton nuclear magnetic resonance Spectrum, $d_6$-DMSO (ppm): 1.09 t, 2H (1/3 Et); 3.00 s, 8H ($CH_2$); 3.36 q, 4/3 H (1/3 Et); 3.84 s, 4H ($CH_2$); 4.85 s, 2H ($COCH_2O$); 6.80–8.22 m, 14H (Ar+$NH_3^+$); 10.86 s 1H (NH).

Melting point: 220° C.

EXAMPLE 5

4-(2,3-Xylyl)-1-(tryptamine-5-O-carboxymethyl) piperazide hydrochloride

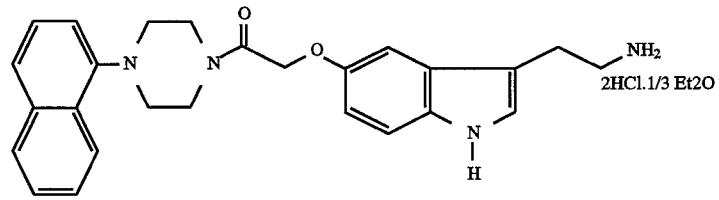

4

2HCl.1/3 Et2O

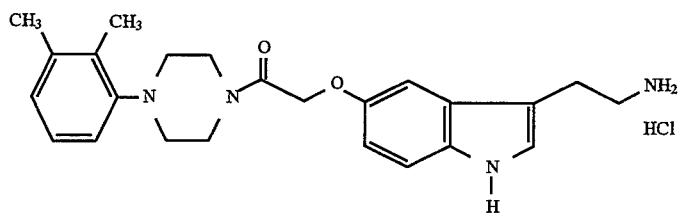

5A 4-(2,3-Xylyl)-1-(tert-butoxycarbamate-tryptamine-5-O-carboxymethyl)piperazide hydrochloride

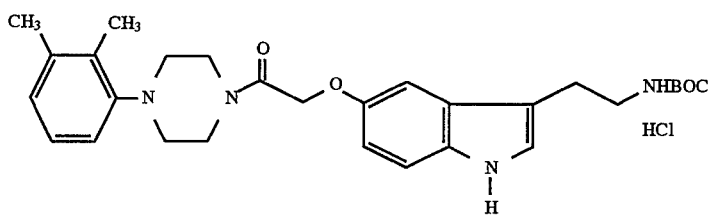

The compound 5A is obtained from 1-(2,3-xylyl) piperazine (343 mg; 1.8 mmol), chloroacetyl chloride (0.143 ml; 1.8 retool) and the tert-butoxycarbamate of 5-hydroxytryptamine 1A (276 mg; 1.0 mmol) according to the procedure described in the preparation of the compound 2B. The purification of the product in the base form is carried out by chromatography on a column of silica gel eluted with a dichloromethane/acetone (20:1; v/v) and then (10:1; v/v) mixture. The pure product is isolated in the form of a colorless syrup which leads, after treatment with hydrochloric acid in ether, to the expected compound.

Elemental analysis ($C_{29}H_{39}N_4Cl$), % calculated: C 64.13; H 7.24; N 10.32; % found: C 63.43; H 7.35; N 10.01.

Proton nuclear magnetic resonance spectrum, $d_6$-DMSO (ppm): 1.37 s, 9H (tBu); 2.21 s, 6H ($CH_3$); 2.75 m, 6H ($CH_2$); 3.18 s, 2H ($CH_2$); 3.68 s, 4H ($CH_2$); 4.80 s, 2H ($COCH_2O$); 6.74–7.25 m, 7H (Ar); 10.68 s, 1H (NH).

Melting point: 90° C.

5—4-(2,3-Xylyl)-1-(tryptamine-5-O-carboxymethyl)piperazide hydrochloride:

The compound 5A, in the base form (173 mg; 0.34 mmol), treated under the conditions described in the preparation of the product 1 from the product 1D and purified under the same conditions, makes it possible to obtain a colorless syrup (108 mg; 78%).

This syrup leads to the bishydrochloride 5 by addition of the necessary amount of hydrochloric acid in ether.

Elemental analysis ($C_{24}H_{32}Cl_2N_4O_2 \cdot 1/3 Et_2O$), % calculated: C 60.12; H 6.73; N 11.69; % found: C 61.22; H 7.07; N 11.31.

Proton nuclear magnetic resonance spectrum, $d_6$-DMSO (ppm): 2.22 s, 6H ($CH_3$); 2.81–3.00 m, 8H ($CH_2$); 3.70 s, 4H ($CH_2$); 4.82 s, 2H ($OCH_2CO$); 6.77–7.29 m, 7H (Ar); 8.08 s, 3H ($NH_3^+$); 10.86 s, 1H (NH).

Melting point: 132° C.

EXAMPLE 6

4-(m-Methoxyphenyl)-1-(tryptamine-5-O-carboxymethyl) piperazide hydrochloride:

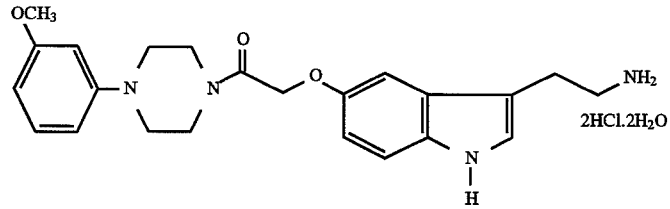

6A—4-(m-Methoxyphenyl)-1-(tert-butoxycarbamate-tryptamine-5-carboxymethyl)piperazide hydrochloride:

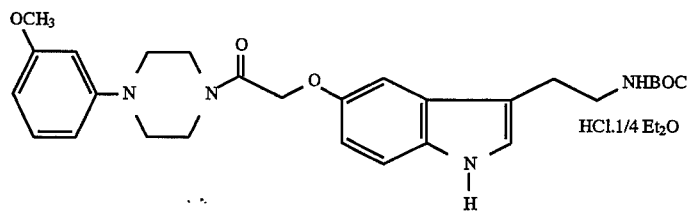

The compound 6A is obtained from (m-methoxyphenyl) piperazine (300 rag; 1.56 ml), chloroacetyl chloride (0.124 ml; 1.56 mmol) and the tert-butoxycarbamate of 5-hydroxytryptamine 1A (237 mag; 0.86 mmol) according to the procedure described in the preparation of the compound 2B (Method A). The purification of the product in the base form is carried out by chromatography on a column of silica gel eluted with a dichloromethane/acetone (10:1, v/v) mixture. The pure product is isolated in the form of a colorless syrup which leads, after treatment with hydrochloric acid in ether, to the expected compound (707 mg; 78%).

Elemental analysis ($C_{28}H_{37}Cl_2N_4O_5$. 1/4$Et_2O$), % calculated: C 59.89; H 7.19; N 9.63; % found: C 59.97; H 6.87; N 9.62.

Proton nuclear magnetic resonance spectrum, $d_6$-DMSO (ppm): 1.09 t, 3/2 H ($Et_2O$); 1.37 s, 9H (tBu); 2.74 m, 2H ($CH_2$); 3.32 m, 7H ($CH_2$ +$Et_2O$); 3.74 s, 6H ($CH_2$+$H_2O$); 4.81 s, 2H ($OCH_2CO$); 6.55–7.25 m, 9H (Ar +NH); 10.70 s, 1H (NH).

Melting point: 146° C.

6 —1-(Tryptamine-5-O-carboxymethyl)-4-(m-methoxyphenyl)piperazide hydrochloride:

This compound is obtained from the product 6A (154 mg; 0.302 mmol) according to the procedure described in the preparation of the product 1 from 1D. The purification of the product in the base form is carried out by chromatography on a column of silica gel eluted with a chloroform/methanol/aqueous ammonia (80:19:1, v/v) mixture. A colorless syrup is obtained (11 mg; 91%).

This syrup leads to the bishydrochloride by addition of the necessary amount of hydrochloric acid in ether.

Proton nuclear magnetic resonance spectrum, d6-DMSO (ppm): 3.00 s, 4H ($CH_2$); 3.26 d, 4H ($CH_2$); 3.74 s, 7H ($CH_2$+$OCH_3$); 4.83 s, 2H ($OCH_2CO$); 6.54–7.28 m, 8H (Ar); 8.16 s, 3H (NH); 10.86 s, 1H (NH).

EXAMPLE 7

4-Methyl-1- (tryptamine-5-O-carboxymethyl) piperazide hydrochloride:

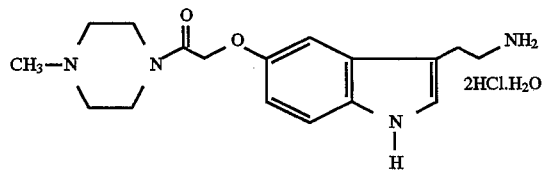

7A—4-Methyl-1-(tert-butoxycarbamate-tryptamine-5-O-carboxymethyl)piperazide hydrochloride:

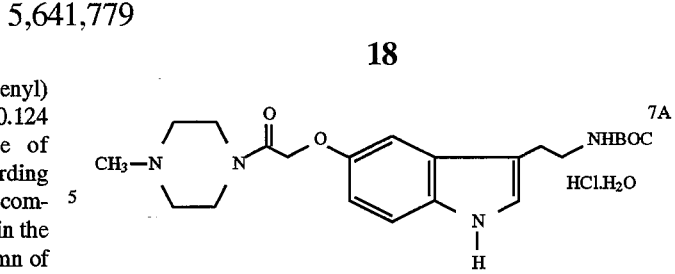

The compound 7A is obtained from methylpiperazine (300 mg; 3.00 mmol), chloroacetyl chloride (0.239 ml; 3.0 mmol) and the tert-butoxycarbamate of 5-hydroxytryptamine 1A (455 mg; 1.65 mmol) according to the procedure described in the preparation of the compound 2B (Method A). The purification of the product in the base form is carried out by chromatography on a column of silica gel eluted with a dichloromethane/methanol (10:1; v/v) mixture. The pure product is isolated in the form of a colorless syrup which leads, after treatment with hydrochloric acid in ether, to the expected compound (918 mg, 65 %).

Elemental analysis ($C_{22}H_{35}ClN_4O_5$), % calculated: C 56.10; H 7.49; N 11.90; % found: C 57.21; H 7.50; N 11.51.

Proton nuclear magnetic resonance spectrum, $d_6$-DMSO (ppm): 1.36 s, 9H (tBu); 2.75 s, 5H; 3.21 m, 10H; 4.80 s, 2H ($OCH_2CO$); 6.74–7.25 m, 5H (Ar +NH); 10.69 s, 1H (NH); 11.28 s, 1H (NH).

Melting point: 204° C.

7—4-Methyl-1-(tryptamine-5-O-carboxymethyl)piperazide hydrochloride:

This compound is obtained from the compound 7A (150 mg; 0.36 mmol) according to the procedure described in the preparation of the product 1 from the product 1D. The purification of the product in the base form is carried out by chromatography on a column of silica gel eluted with a chloroform/methanol/aqueous ammonia (80:19:1; v/v) mixture. A colorless syrup is obtained (102 mg; 79%).

The bishydrochloride is obtained by addition of the necessary amount of hydrochloric acid in ether.

Proton nuclear magnetic resonance spectrum, $d_6$-DMSO (ppm): 2.77 s, 3H 3.00–3.57 m, 10H ($CH_2$); 4.15–4.37 m, 2H; 4.85 s, 2H ($COCH_2$); 6.80 dd, 1H (Ar); 7.23 m, 3H; (Ar); 8.18 s, 3H ($NH_3^+$); 10.86 s, 1H (NH); 11.39 s, 1H (NH).

EXAMPLE 8

1-[(tert-Butoxycarbamate) tryptamine-5-O-carboxymethyl]-4 -[10 -(8-methylthio-10-11-dihydrodibenzo[b, f]thiepine)]piperazide hydrochloride:

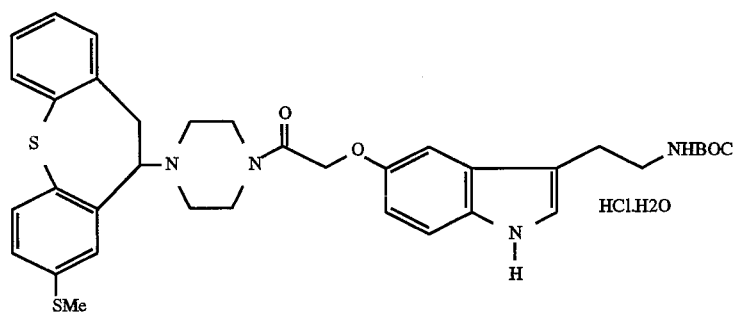

This compound is obtained from 8-methylthio-10-piperazino-10-11-dihydrodibenzo[b,f] thiepin (Protiva et al., Collection Czechoslov. Chem. Commun., 36, 2226–2247, 1971) (300 mg, 0.876 mmol), chloroacetyl chloride (0.069 ml; 0.876 mmol) and the tert-butoxycarbamate of 5-hydroxytryptamine 1A (132 mg; 0.48 mmol) according to the procedure described in the preparation of the compound 2B (Method A). The purification of the product in the base form is carried out by chromatography on a column of silica gel eluted with a dichloromethane/ethyl acetate (5:1; v/v) mixture. The pure product is isolated in the form of a colorless syrup (420 mg; 74%). The hydrochloride is obtained by addition of the necessary amount of hydrochloric acid in ether.

Elemental analysis ($C_{36}H_{43}N_4O_4S_2Cl$); % calculated: C 60.61; H 6.35; N 7.85; % found: C 61.15; H 6.65; N 7.52.

Proton nuclear magnetic resonance spectrum, $d_6$-DMSO (ppm): 1.37 s, 9H (tBu); 2.74 m, 2H; 3.17–3.99 m, 13H ($CH_2$); 4.78 s, 2H ($OCH_2CO$); 5.26 s, 1H (Ar); 10.69 s, 1H (NH); 1.46 s, 1H (NH).

Melting point: 158° C.

Example 9
4-O-Tolyl-1-[tryptamine-5-O-(α-phenylcarboxymethyl)]piperazide hydrochloride:

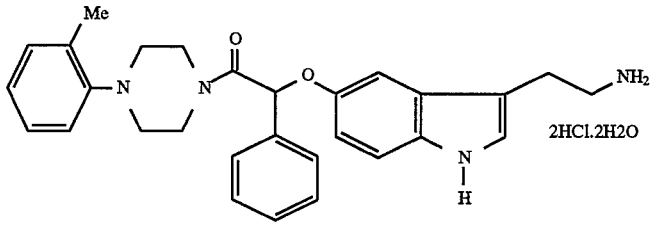

The compound 9 is obtained from 4-(o-tolyl)piperazine (2.5 g; 14.3 mmol), α-chlorophenylacetyl chloride (2.26 ml; 14.3 mmol) and the tert-butoxycarbamate of 5-hydroxytryptamine 1A (2.17 g; 7.86 mmol) according to the procedure described in the preparation of Example 2. The purification of the product in the base form is carried out by chromatography on a column of silica gel eluted with a chloroform/methanol/aqueous ammonia (80:19:1, v/v) mixture. The pure product is isolated in the form of a colorless syrup (58%). The hydrochloride is obtained by addition of the necessary amount of hydrochloric acid in ether.

Elemental analysis ($C_{29}H_{36}N_4O_3Cl_2$); % calculated: C 63.79; H 6.50; N 10.26; % found: C 63.83; H 6.61; N 10.00

Proton nuclear magnetic resonance spectrum, d6-DMSO (ppm): 2.24 s, 3H ($CH_3$); 2.75 m, 4H ($CH_2$); 2.99 s, 4H ($CH_2$); 3.47–3.86 m, 4H ($CH_2$); 6.34 s, 1H (CH); 6.83–7.62 m, 13H (Ar); 8.11 s, 3H ($NH_3^+$); 10.88 s, 1H (NH).

Melting point: 164° C.

EXAMPLE 10

4-Naphthyl-1-[tryptamine-5-O-(α-phenylcarboxymethyl)]piperazide hydrochloride:

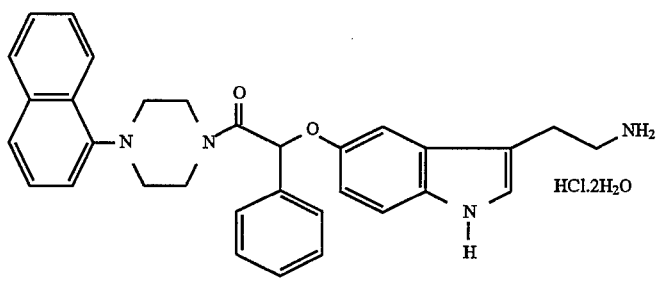

The compound 10 is obtained from naphth-1-yl-piperazine (0.60 g; 4.18 mmol), α-chlorophenylacetyl chloride (0.66 ml; 4.18 mmol) and the tert-butoxycarbamate of 5-hydroxytryptamine 1A (0.63 g; 2.30 mmol) according to the procedure described in the preparation of Example 2. The product, in the base form, is purified by chromatography on a column of silica gel eluted with a chloroform/methanol/ aqueous ammonia (80:19:1, v/v) mixture. The pure product is isolated in the form of a colorless syrup (1.03 g; 49% for the 3 stages). The hydrochloride is obtained by addition of the necessary amount of hydrochloric acid in ether.

Elemental analysis ($C_{32}H_{37}N_4O_4Cl$), % calculated: C 66.54; H 6.41; N 9.70; % found: C 67.02; H 6.16; N 9.33

Proton nuclear magnetic resonance spectrum, $d_6$-DMSO (ppm): 2.99 s, 8H ($CH_2$); 4.00 m, 4H ($CH_2$); 8.36 s, 1H (CH); 6.85–7.87 m, 16H (Ar); 8.13 s, 3H ($NH_3^+$); 10.89 s, 1H (NH).

Melting point: 178° C.

EXAMPLE 11

4-o-Tolyl-1-[tryptamine-5-O-(α-methylcarboxymethyl)]piperazide hydrochloride:

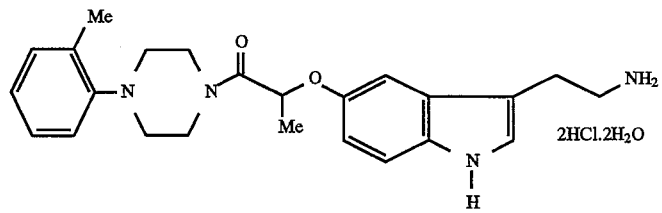

11

2HCl.2H₂O

The compound 11 is obtained from 4-(o-tolyl)piperazine (0.40 g; 2.26 mmol), α-methylchloroacetyl chloride (0.22 ml; 2.26 mmol) and the tert-butoxycarbamate of 5-hydroxytryptamine 1A (0.34 g; 1.24 mmol) according to the procedure described in the preparation of Example 2. The product 11, in the base form, is purified by chromatography on a column of silica gel eluted with a chloroform/methanol/aqueous ammonia (80:18.5:1, v/v) mixture. The pure product is isolated in the form of a colorless syrup (269 mg; 30% for the 3 stages). The hydrochloride is obtained by addition of the necessary amount of hydrochloric acid in ether.

Elemental analysis ($C_{24}H_{36}N_4O_4Cl_2$), % calculated: C 55.92; H 7.03; N 10.86; % found: C 56.54; H 6.83; N 10.62.

Proton nuclear magnetic resonance spectrum, $d_6$-DMSO (ppm): 1.45 d, 3H ($CH_3$); 2.28 s, 3H ($CH_3$); 2.81 s, 4H ($CH_2$); 2.99 s, 4H ($CH_2$); 3.62–3.77 m, 4H ($CH_2$); 5.28 q, 1H (CH); 6.75 dd, 1H: 6.95–7.29 m, 7H (Ar); 8.09 s, 3H ($NH_3^+$); 10.88 s, 1H (NH).

Melting point: 153°–154° C. (polymorphism).

EXAMPLE 12

4-(Naphth-1-yl)-1-(tryptamine-5-O-methylsulfonyl) piperazide hydrochloride:

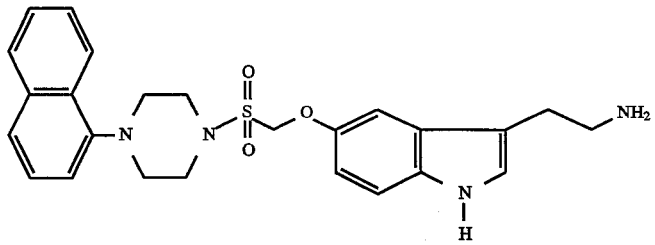

12

The compound 12 is obtained from 1-naphthylpiperazine (800 mg; 3.76 mmol), chloromethanesulfonyl chloride (561 mg; 3.76mmol) and the tert-butoxycarbamate of 5-hydroxytryptamine 1A (520 mg; 2.07 mmol) according to the procedure described in the preparation of Example 2. The purification of the product in the base form is carried out by chromatography on a column of silica gel eluted with a chloroform/methanol/aqueous ammonia (80:19:1; v/v) mixture. The pure product is isolated in the form of a colorless syrup which leads, after treatment with hydrochloric acid in ether, to the expected compound (580 mg; 56%).

EXAMPLE 13

4-m-Chlorophenyl-1-(tryptamine-5-O-propyl) piperazine hydrochloride:

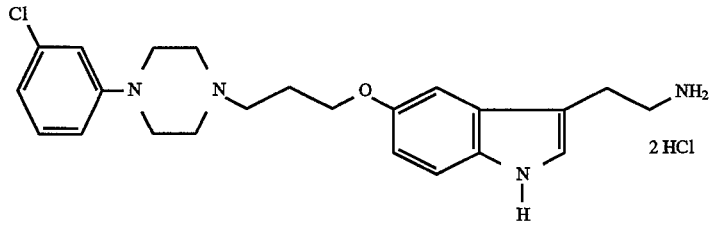

13

2 HCl

13A—4-m-Chlorophenyl-1-(tert-butoxycarbamate-tryptamine-5-O-propyl)piperazine:

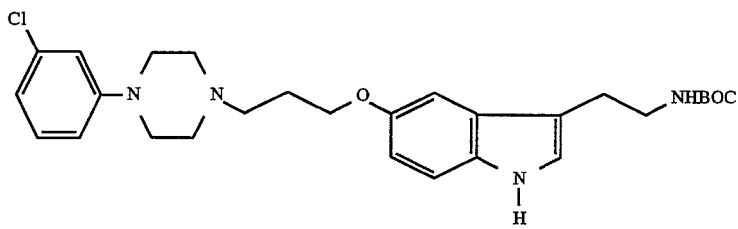

A mixture of 1-(3-chlorophenyl)-4-(3-chloropropyl) piperazine (700 rag; 2.56 retool) and the tert-butoxycarbamate of 5-hydroxytryptamine 1A (353 mg; 1.28 mmol) in dimethylformamide (6 ml) in the presence of potassium iodide (425 mg; 2.56 mmol) and potassium carbonate (530 mg; 3.84 mmol) is heated at 100° C. for 7 hours. The mixture is then diluted with ether and washed with water and then with a saturated sodium chloride solution. The organic phase is dried over sodium sulfate, filtered and then evaporated to dryness. The syrup obtained is chromatographed on a column of silica gel eluted with a dichloromethane/methanol (20:1; v/v) mixture. The pure compound is isolated in the form of a syrup (426 mg; 65%).

13—4-m-Chlorophenyl-1-(tryptamine-5-0-propyl) piperazine hydrochloride:

The compound 13A (200 mg; 0.39 mmol), treated under the conditions described in the preparation of the product 1 from the product 1D and purified under the same conditions, makes it possible to obtain a colorless syrup (133 mg; 75%).

This syrup leads to the hydrochloride 13 by addition of the necessary amount of hydrochloric acid in ether.

EXAMPLE 14

4-(4-Acetylphenyl)-1-(tryptamine-5-O-carboxymethyl)piperazide hydrochloride:

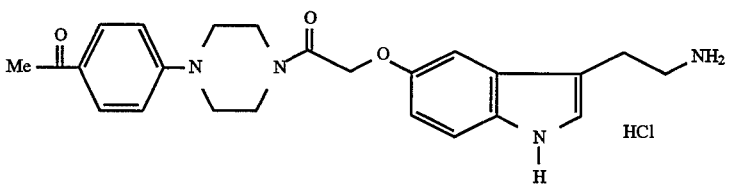

The compound 14 is obtained from 4'-piperazinoacetophenone (531 mg; 2.44 mmol), chloroacetyl chloride (0.194 ml; 2.44 mmol) and the tert-butoxycarbamate of 5-hydroxytryptamine 1A (374 mg; 1.35 mmol according to the procedure described in the preparation of Example 2. The purification of the product in the base form is carried out by chromatography on a column of silica gel eluted with a chloroform/methanol/aqueous ammonia (80:19:1; v/v) mixture. The pure product is isolated in the form of a yellow syrup which leads, after treatment with hydrochloric acid in ether, to the expected compound (307 mg; 45%).

Elemental analysis: ($C_{24}H_{29}N_4O_3Cl$), % calculated: C 63.08; H 6.40; N 12.26; % found: C 62.86; H 6.55; N 12.03.

Proton nuclear magnetic resonance spectrum, $d_6$-DMSO (ppm): 2.46 s, 3H ($CH_3$); 2.92–3.02 m, 4H ($CH_2$); 3.37 m, 4H ($CH_2$); 3.63 m, 4H ($CH_2$); 4.83 s, 2H ($COCH_2O$); 6.77–7.29 m, 6H (Ar); 7.69–7.85 m, 5H (Ar +$NH_3^+$); 10.85 s, 1H (NH).

Melting point: 155° C (dec.).

EXAMPLE 15

4-(2,4-Dimethylphenyl)-1-(tryptamine-5-O-carboxymethyl)piperazide hydrochloride:

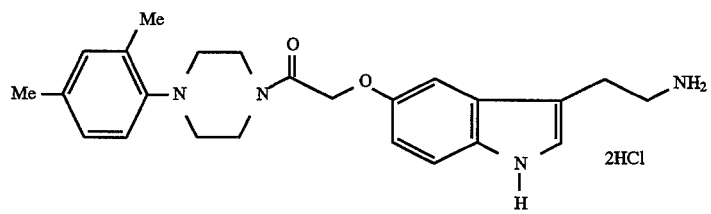

The compound 15 is obtained from 1-(2,4-dimethylphenyl)piperazine (1000 mg; 5.26 mmol), chloroacetyl chloride (0.419 ml); 5.26 mmol) and the tert-butoxycarbamate of 5-hydroxytryptamine 1A (682 mg; 2.47 mmol) according to the procedure described in the preparation of Example 2. The purification of the product in the base form is carried out by chromatography on a column of silica gel eluted with a chloroform/methanol/aqueous ammonia (80:18:2; v/v) mixture. The pure product is isolated in the form of a colorless syrup which leads, after treatment with hydrochloric acid in ether, to the expected compound (720 mg; 71%).

Elemental analysis ($C_{24}H_{32}N_4O_2Cl_2$), % calculated: C 60.12, H 6.73; N 11.69; % found: C 59.85; H 6.99; N 11.58.

Proton nuclear magnetic resonance spectrum, $d_6$-DMSO (ppm): 2.23 s, 3H ($CH_3$); 2.29 s, 3H ($CH_3$); 2.89–3.00 m, 8H ($CH_2$); 3.70 m, 4H ($CH_2$); 4.83 s, 2H ($COCH_2$); 6.77–7.29 m, 7H (Ar); 8.11 s, 3H ($NH_3^+$); 10.87–10.88 d, 1H (NH).

Melting point: 162° C.

EXAMPLE 16

4-(4-Chlorophenyl)-1-(tryptamine-5-O-carboxymethyl)piperazide hydrochloride:

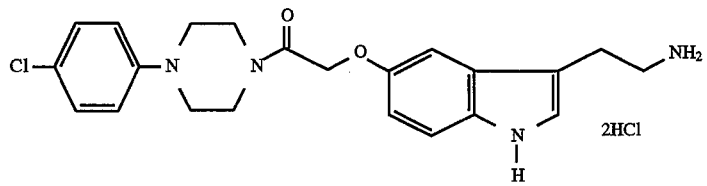

The compound 16 is obtained from 1-(4-chlorophenyl)piperazine (2.5 g; 12.71 mmol), chloroacetyl chloride (1.25 ml; 15.26 mmol) and the tert-butoxy- carbamate of 5-hydroxytryptamine 1A (1.53 g; 5.55 mmol) according to the procedure described in the preparation of Example 2. The purification of the product in the base form is carried out by chromatography on a column of silica gel eluted with a chloroform/methanol/aqueous ammonia (80:19:1; v/v) mixture. The pure product is isolated in the form of a colorless syrup which leads, after treatment with hydrochloric acid in ether, to the expected compound (1.48 g; 55%).

Elemental analysis ($C_{22}H_{27}N_4O_2Cl_3$), % C 54.39; H 5.60; N 11.53; % found: C 53.96; H 5.58; N 11.11.

Proton nuclear magnetic resonance spectrum, $d_6$-DMSO (ppm): 2.99–3.22 m, 8H ($CH_2$); 3.67 m, 4H ($CH_2$); 4.83 s, 2H ($COCH_2O$); 6.77–7.30 m, 8H (Ar); 8.10 s, 3H ($NH_3^+$); 10.86 s, 1H (NH).

Melting point: 259° C.

EXAMPLE 17

4-(3,4-Dichlorophenyl)-1-(tryptamine-5-O-carboxymethyl)piperazide hydrochloride:

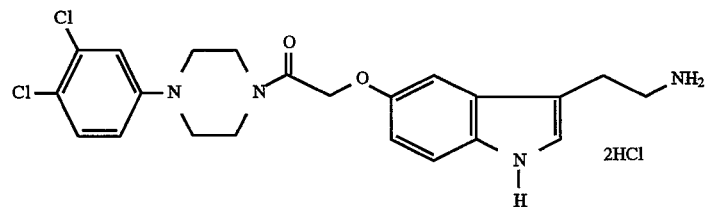

The compound 17 is obtained from 1-(3,4-dichlorophenyl)piperazine (600 mg; 2.60 mmol), chloroacetyl chloride (0. 207 ml; 2.60 mmol) and the tert-butoxycarbamate of 5-hydroxytryptamine 1A (420 mg; 1.52 mmol) according to the procedure described in the preparation of Example 2. The purification of the product in the base form is carried out by chromatography on a column of silica gel eluted with a chloroform/methanol/aqueous ammonia (80:19:1; v/v) mixture. The pure product is isolated in the form of a colorless syrup which leads, after treatment with hydrochloric acid in ether, to the expected compound (584 mg; 74%).

Elemental analysis ($C_{22}H_{26}N_4O_2Cl_4H_2O$), % calculated: C 48.44; H 5.32; N 10.27; % found: C 48.53; H 5.02; N 9.98.

Proton nuclear magnetic resonance spectrum, $d_6$-DMSO (ppm): 3.00–3.27 m, 8H ($CH_2$); 3.65 m, 4H ($CH_2$); 4.82 s, 2H ($COCH_2$); 6.77–7.44 m, 7H (Ar); 8.15 s, 3H ($NH_3^+$); 10.86 s, 1H (NH).

Melting point: 179°–181 C.

EXAMPLE 18

4-(4-Methoxyphenyl)-1-(tryptamine-5-O-carboxymethyl)piperazide hydrochloride:

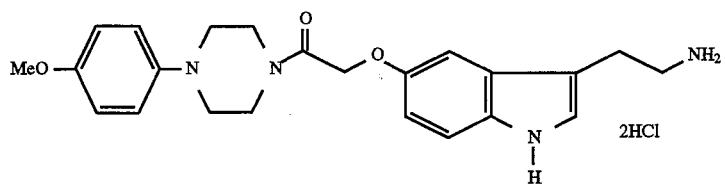

The compound 18 is obtained from 1-(4-methoxyphenyl)piperazine (600 mg; 3.12 mmol), chloroacetyl chloride (0.25 ml; 3.12 mmol) and the tert-butoxycarbamate of 5-hydroxytryptamine 1A (362 mg; 1.31 mmol) according to the procedure described in the preparation of Example 2. The purification of the product in the base form is carried out by chromatography on a column of silica gel eluted with a chloroform/methanol/aqueous ammonia (80:19.5:0.5; v/v) mixture. The pure product is isolated in the form of a colorless syrup which leads, after treatment with hydrochloric acid in ether, to the expected compound (455 mg; 53%).

Elemental analysis ($C_{23}H_{30}N_4O_3Cl_2$. $1.7H_2$), % calculated: C 53.95; H 6.57; N 10.94; % found: C 54.41; H 6.29; N 10.47.

Proton nuclear magnetic resonance spectrum, $d_6$-DMSO (ppm): 3.00 s, 4H ($CH_2$); 3.38 m, 4H ($CH_2$); 3.76 s, 3H (OMe); 3.95 m, 4H ($CH_2$); 4.87 s, 2H ($COCH_2O$); 6.78–7.53 m, 8H (Ar); 8.09 s, 3H ($NH_3^+$); 10.86 s, 1H (NH).

Melting point: 170 ° C.

EXAMPLE 19

4-Cyclopentyl-1-(tryptamine-5-O-carboxymethyl) piperazide hydrochloride:

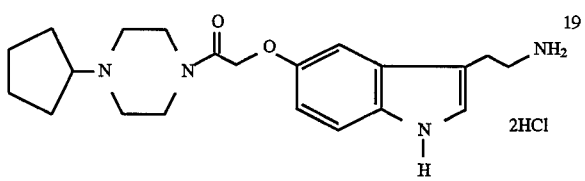

The compound 19 is obtained from 1-cyclopentylpiperazine (1000 mg; 6.48 mmol), chloroacetyl chloride (0.516 ml; 6.48 mmol) and the tert-butoxycarbamate of 5-hydroxytryptamine 1A (702 mg; 2.54 mmol) according to the procedure described in the preparation of Example 2. The purification of the product in the base form is carried out by chromatography on a column of silica gel eluted with a chloroform/methanol/aqueous ammonia (80:19:1; v/v) mixture. The pure product is isolated in the form of a colorless syrup which leads, after treatment with hydrochloric acid in ether, to the expected compound (467 mg; 41%).

Elemental analysis ($C_{21}H_{32}N_4O_2Cl_2 \cdot 0.7H_2O$), % calculated: C 55.31; H 7.38; N 12.29; % found: C 55.44; H 7.03; N 12.03.

Proton nuclear magnetic resonance spectrum, $d_6$-DMSO (ppm): 1.42–2.10 m, 8H ($CH_2$); 2.99–3.63 m, 11H; 4.12–4.38 m, 2H; 4.85 S, 2H ($COCH_2O$); 6.78–7.29 m, 4H (Ar); 8.05 s, 3H ($NH_3^+$); 10.85 s, 1H (NH); 11.32 s, 1H.

Melting point: 195° (dec.).

EXAMPLE 20

4-o-Tolyl-1-(tryptamine-5-ethoxy)piperazide hydrochloride:

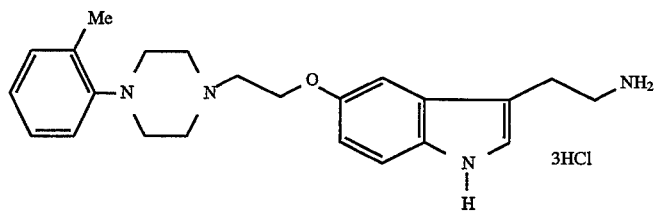

20A—tert-Butoxycarbamate of 5-(2-chloroethoxy) tryptamine:

The product 1A (5 g; 18.09 mmol) in solution in methyl ethyl ketone (25 ml), in the presence of potassium carbonate (15 g; 108.5 mmol), is treated with 1-bromo-2-chloroethane. After 24 hours at reflux, the mixture is diluted with dichloromethane, filtered on celite and evaporated to dryness. The brown syrup obtained is chromatographed on a column of silica gel eluted with a dichloromethane/acetone (30:1, v/v) mixture. The pure product is obtained in the form of white crystals (5.2 g; 84%).

Elemental analysis ($C_{17}H_{23}N_2O_3Cl_3$), % calculated: C 60.26; H 6.84; N 8.27; % found: C 60.37; H 6.98; N 8.21.

Proton nuclear magnetic resonance spectrum, $d_6$-DMSO (ppm): 1.46 s, 9H (tBu); 2.88–2.95 t, 2H ($CH_2$); 3.45 m, 2H ($CH_2$); 3.81–3.87 t, 2H ($CH_2$); 4.26–4.32 t, 2H ($CH_2$); 4.65 s, 1H (NH); 6.87–6.93 dd, 1H (Ar) 7.01–7.29 m, 3H (Ar); 8.16 s, 1H (NH)

Melting point: 129° C.

EXAMPLE 20

4-(o-Tolyl)-1-(tryptamine-5-ethoxy)piperazide hydrochloride:

A mixture of the product 20A (576 mg; 1.70 mmol) and of ortho-tolylpiperazine (300 mg; 1.70 mmol) in dimethylformamide (0.8 ml) in the presence of potassium carbonate (705 mg; 5.1 mmol) and of potassium iodide (28 mg; 0.17 mmol) is heated at 80° C. for 27 hours. The mixture is then diluted with ethyl acetate, filtered on cotton and washed with water and then with a saturated sodium chloride solution. The organic phase is dried over sodium sulfate, filtered and evaporated to dryness. The syrup obtained is purified on a column of silica gel eluted with a dichloromethane/methanol (30:1, v/v) mixture. The pure product is isolated in the form of a beige foam (676 mg; 83%).

This product is deprotected according to the method described in the preparation of Example 1 from 1D. The syrup obtained is chromatographed on a column of silica gel eluted with a dichloromethane/methanol/aqueous ammonia (80:19:1, v/v) mixture.

The pure product is isolated in the form of a colorless syrup which leads, after treatment with hydrochloric acid in ether, to the compound 20 (644 mg; 89%).

Elemental analysis ($C_{23}H_{33}N_4O_1Cl_3$), % calculated: C 56.62; H 6.82; N 11.48; % found: C 56.53; H 6.99; N 11.16.

Proton nuclear magnetic resonance spectrum, $d_6$-DMSO (ppm): 2.27 s, 3H (Me); 3.02–3.37 m, 6H ($CH_2$); 3.63–3.68 m, 4H ($CH_2$); 4.03 s, 4H ($CH_2$); 4.51 m, 2H ($CH_2$); 6.80–7.32 m, 8H (Ar); 8.17 s, 3H ($NH_3^+$); 10.92–10.93 d, 1H (NH); 11.44 s, 1H ($NH^+$).

Melting point: 149°–151° C.

EXAMPLE 21

4-(Naphth-1-yl)-1-(tryptamine-5-ethoxy)piperazide hydrochloride:

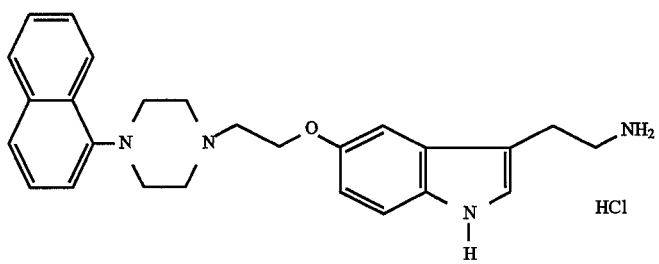

21

The compound 21 is obtained from the compound 20A (1388 mg; 4.09 mmol) and from 1-naphthylpiperazine (870 mg; 4.09 mmol) according to the procedure described in the preparation of Example 20. The purification of the product in the base form is carried out by chromatography on a column of silica gel eluted with a chloroform/methanol/ aqueous ammonia (85:14:1; v/v) mixture. The pure product is isolated in the form of a colorless syrup which leads, after treatment with hydrochloric acid in ether, to the expected compound (1064 mg; 72%).

Elemental analysis ($C_{26}H_{31}N_4O_1Cl_1$), % calculated: C 69.24; H 6.93; N 12.42; Cl 1 7.86; % found: C 68.78; H 6.85; N 12.26; Cl 7.25.

Proton nuclear magnetic resonance spectrum, $d_6$-DMSO (ppm): 2.85–3.37 m, 14H ($CH_2$); 4.15–4.21 t, 2H ($CH_2$); 6.78–8.16 m, 13H (Ar +$NH_3^+$); 10.86 s, 1H (NH).

Melting point: 122° C.

EXAMPLE 22

4-(3,4-Dichlorophenyl)-1-(tryptamine-5-ethoxy) piperazide hydrochloride:

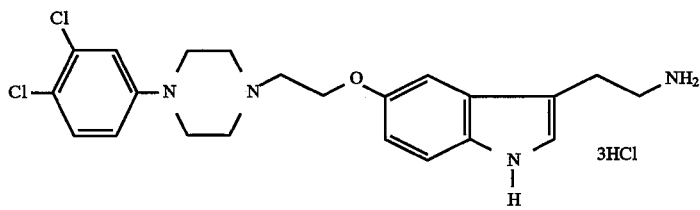

22

The compound 22 is obtained from the compound 20A (1000 mg; 2.95 mmol) and from (3,4-dichlorophenyl) piperazine (682 mg; 2.95 mmol) according to the procedure described in the preparation of Example 20. The purification of the product in the base form is carried out by chromatography on a column of silica gel eluted with a chloroform/ methanol/aqueous ammonia (80:19:1; v/v) mixture. The pure product is isolated in the form of a beige syrup which leads, after treatment with hydrochloric acid in ether, to the expected compound (1.11 g; 75%).

Elemental analysis ($C_{22}H_{29}N_4O_1Cl_5$), % calculated: C 48.69; H 5.39; N 10.32; Cl 32.66% found: C 48.16; H 5.38; N 10.02; Cl 1 30.82.

Proton nuclear magnetic resonance spectrum, $d_6$-DMSO (ppm): 3.00–3.94 m, 14H ($CH_2$); 4.85 d, 2H ($CH_2$); 6.77–7.47 m, 7H (Ar); 8.19 s, 3H ($NH_3^+$); 10.92 s, 1H (NH); 11.62 s, 1H (NH).

Melting point: 154° C.

STUDY OF AFFINITY FOR 5-$HT_{1D}$ RECEPTORS

This study is carried out according to the technique described by Herrick-Davis and Titeler (J. Neurochem. 50, 1624–1631, 1988).

Preparation of the membranes:

Sheep brains are removed at the local abattoir and transported in ice. The caudate nuclei are removed, weighed and homogenized with a Polytron for 20 sec. (speed 6–7) in 20 volumes of Tris-HCl 50 mM, pH 7.7. The homogenate is centrifuged for 10 min at 48,000 g with an L5 50E centrifuge (Beckman).

The pellet, taken up in 20 volumes of Tris-HCl 50 mM, pH 7.7, is placed in a water bath at 37° C. for 10 min and then recentrifuged for 10 min at 48,000 g. The pellet then obtained is immediately frozen in fractions containing 0.5 g of tissue.

Affinities:

The pellet is defrosted and homogenized with a Dounce in 80 volumes of Tris-HCl, 50 mM pH 7.7 containing 4 mM $CaCl_2$, 10μM of pargyline and 0.1% of ascorbic acid.

Binding is carried out at 25° C. by incubating for 30 min:

0.1 ml of buffer or 10 μM, as final concentration, of sumatriptan, in order to obtain the non-specific binding, or the product which forms part of this invention at various concentrations (between $10^{-10}$ and $10^{-6}$M).

0.8 ml of membrane suspension 0.1 ml of $^3$H-5-HT (15 to 30 Ci/mM, New England Nuclear France)

The incubation is brought to an end by rapid filtration through GF/B filters and rinsing with 3 times 3 ml of ice-cold buffer, using a harvester manufactured by Brandel which makes it possible to filter 48 samples. The filters are introduced into vials containing 4 ml of emulsifier-safe liquid scintillant (Packard) and the radioactivity measured with a Tri-carb 4640 counter (Packard).

The $IC_{50}$ (concentration which inhibits the specific affinity by 50%) is determined graphically.

The $IC_{50}$ values of the various products which form part of this invention for the other receptors were measured according to the techniques described in the following references:

5-$HT_{1A}$ and $_B$ Receptors

Peroutka S. J. Pharmacological differentiation and characterization of 5-$HT_{1A}$, 5-$HT_{1B}$ and 5-$HT_{1C}$ binding sites in rat frontal cortex. J. Neurochem., 45, 529–540, 1986.

5-$HT_{1C}$ Receptor

Pazos A., Hoyer D. and Palacios J. M. The binding sites of serotonergic ligands to the porcine choroid plexus:

characterization of a new type of serotonin recognition site. Eur. J. Pharmacol., 106, 539–546, 1985.

5-HT$_2$ Receptor

Leysen J. E., Niemegeers C. J. E., Van Nueten J. M. and Laduron P.M. $^3$H-ketanserine (R 41468), a selective $^3$H ligand for serotonin2 receptor binding sites. Mol. Pharmacol., 21, 301–330, 1982.

α1-Adrenergic receptor

Leslie Morrow A. and Creese I. Characterization of α1-adrenergic receptor subtypes in rat brain: a reevaluation of $^3$H-WB4101 and $^3$H prazosin binding. Mol. Pharmacol. 29, 321–330, 1986.

α2-Adrenergic receptor

Mallard N. J., Tyacke R., Hudson A. L. and Nutt D. S. Comparative binding studies of $^3$-idazoxan and $^3$-RX821002 in the rat brain. Brit. J. Pharmacol. 102, 221P, 1991.

D2-Dopaminergic receptor

Nisnik H. B., Grigoriadis D. E., Pri-Bar I., Buckman O. and Seeman P. Dopamine D2 receptors selectively labeled by a benzamide neuroleptic: $^3$H-YM-09159-2 Naunyn-Schmiedeberg's Arch. Pharmacol. 329, 333–343, 1985.

behavior, anxiety, migraine, Alzheimer's disease and memory disorders.

The present invention also relates to the medicaments comprising at least one compound of formula (I) in the pure state or in the form of a composition in which it is combined with any other pharmaceutically compatible product, which can be inert or physiologically active. The medicaments according to the invention can be employed orally, parenterally, rectally, topically or by any other administration route.

Tablets, pills, powders (gelatin capsules or cachets) or granules can be used as solid compositions for oral administration. In these compositions, the active principle according to the invention is mixed with one or a number of inert diluents, such as starch, cellulose, sucrose, lactose or silica, under an argon stream. These compositions can also comprise substances other than the diluents, for example one or a number of lubricating agents such as magnesium stearate or talc, a coloring agent, a coating agent (dragées) or a varnish.

Pharmaceutically acceptable solutions, suspensions, emulsions, syrups and elixirs containing inert diluents such as water, ethanol, glycerol, vegetable oils or paraffin oil can be used as liquid compositions for oral administration. These

| | | | | Affinity outline of the molecules (IC50 × 10–9M) | | | | | | | |
|---|---|---|---|---|---|---|---|---|---|---|---|
| | | | | 5-HT$_{1D}$ | | 5-HT$_{1A}$ | | 5-HT$_{1B}$ | | | Ratio* |
| Example* | α2 | α1 | D2 | mean | STD# | mean | STD# | mean | STD# | 5-HT$_{1C}$ | 5-HT$_2$ | 1A/1D |
| ID | 7000 | 8500 | >100 | 6.5 | 1.5 | 120 | — | — | — | — | 2000 | 18.5 |
| 3 | >1000 | >1000 | >1000 | 7 | 0.7 | 33.5 | 14.8 | 1.9 | 0.1 | 4000 | >1000 | 4.8 |
| 1 | >1000 | >1000 | >1000 | 2.1 | 0.1 | 23.5 | 4.9 | 0.6 | | 3000 | >1000 | 11.2 |
| 4 | >1000 | >1000 | >1000 | 3.2 | 0.2 | 115 | 70.7 | 1.9 | 0.5 | 1800 | >1000 | 35.9 |
| 5 | >1000 | >1000 | >1000 | 29.3 | 26.6 | 240 | 56.6 | 6 | 0.7 | >1000 | >1000 | 8.2 |
| 5A | >1000 | >1000 | >1000 | 2 | 0.3 | 34.5 | 0.7 | 1 | 0.1 | 1000 | >1000 | 17.3 |
| 6A | >1000 | >1000 | >1000 | 16 | 5.7 | 100 | 14.1 | 1.5 | | >1000 | >1000 | 6.3 |
| 7 | >1000 | >1000 | >1000 | 725 | 35.4 | >1000 | | 355 | 148.5 | >1000 | >1000 | >1.4 |
| 6 | >1000 | >1000 | >1000 | 2.9 | 1.0 | 23.5 | 2.1 | 1.1 | 0.7 | >1000 | >1000 | 8.1 |
| 8 | — | — | — | >1000 | | >1000 | | 1000 | | — | — | |
| 9 | >1000 | >1000 | >1000 | 190 | 42.4 | 325 | 7.1 | 85 | 21.2 | 600 | 550 | 1.7 |
| 10 | >1000 | >1000 | >1000 | 710 | 14.1 | 465 | 21.2 | 335 | 233.3 | >1000 | >1000 | 0.7 |
| 11 | — | — | — | 6.0 | — | 125 | — | 5.5 | — | 1000 | >1000 | 20.8 |

*The examples are those described in the text in order to illustrate the invention.
STD corresponds to the standard deviation.
*Ratio of the IC$_{50}$ values of each product for the 5-HT$_{1A}$ and 5-HT$_{1D}$ receptors.

The new indole compounds derived from piperazine which form part of this invention are ligands having an exceptional affinity for the 5-HT$_{1D}$ and 5-HT$_{1B}$ receptors, as is demonstrated by the examples described above. Many compounds which are an integral part of the present invention have the additional advantage of being particularly selective for the 5-HT$_{1D}$ receptor with respect to the 5-HT$_{1A}$, 5-HT$_{1C}$, 5-HT$_2$, α$_1$, α$_2$ and D$_2$ receptors. The selectivity of the compounds of the present invention and in particular their preferential affinity for the 5-HT$_{1D}$ receptor with respect to the 5-HT$_{1A}$ receptor represents a very important advantage with respect to the ligands of the 5-HT$_{1D}$ receptor known to date (cf. Annual Reports in Medicinal Chemistry, vol. 27, chapter 3, p. 25; Academic Press, 1992).

In human therapeutics, the compounds of general formula (I) according to the invention are particularly useful in the treatment and prevention of disorders related to serotonin. These compounds can therefore be used in the treatment and prevention of depression, compulsive obsessional disorders, bulimia, aggressiveness, alcoholism, nicotine addiction, hypertension, nausea, sexual dysfunctioning, asocial compositions can comprise substances other than the diluents, for example wetting, sweetening, thickening, flavoring or stabilizing substances.

The sterile compositions for parenteral administration can preferably be suspensions, emulsions or non-aqueous or aqueous solutions. Water, propylene glycol, a polyethylene glycol, vegetable oils, in particular olive oil, injectable organic esters, for example ethyl oleate, or other suitable organic solvents can be used as solvent or vehicle. These compositions can also contain adjuvants, in particular wetting, isotonizing, emulsifying, dispersing and stabilizing agents. Sterilization can be carried out in several ways, for example by aseptic filtration, by incorporating sterilizing agents in the composition, by irradiation or by heating. They can also be prepared in the form of solid sterile compositions which can be dissolved at the time of use in sterile water or any other injectable sterile medium.

The compositions for rectal administration are suppositories or rectal capsules which contain, besides the active product, excipients such as cocoa butter, semi-synthetic glycerides or poly(ethylene glycol)s.

The compositions for topical administration can be, for example, creams, lotions, eyedrops, mouthwashes, nosedrops or aerosols.

The doses depend on the desired effect, on the duration of treatment and on the administration route used; they are generally between 0.001 g and 1 g (preferably between 0.005 g and 0.25 g) per day, preferably orally, for an adult with unit doses ranging from 0.1 mg to 500 mg of active substance and preferably from 1 mg to 50 mg.

Generally, the doctor will determine the appropriate dosage depending on the age, weight and all the other factors specific to the subject to be treated. The following examples illustrate compositions according to the invention [in these examples, the term "active component" denotes one or a number (generally one) of the compounds of formula (I) according to the present invention]:

Tablets

They can be prepared by direct compression or by passing through a wet granulation. The procedure by direct compression is preferred but it may not be suitable in all cases, depending on the doses and the physical properties of the active component.

| A - By direct compression | |
|---|---|
| | mg for 1 tablet |
| Active component | 10.0 |
| Microcrystalline cellulose, B.P.C. | 89.5 |
| Magnesium stearate | 0.5 |
| | 100.0 |

The active component is passed through a sieve with a mesh size of 250 μm per side, mixing is carried out with the excipients and compression is carried out using 6.0 mm dies. Tablets having other mechanical strengths can be prepared by modifying the compressive weight with use of appropriate dies.

| B - Wet granulation | |
|---|---|
| | mg for one tablet |
| Active component | 10.0 |
| Lactose, Codex | 74.5 |
| Starch, Codex | 10.0 |
| Pregelatinized maize starch, Codex | 5.0 |
| Magnesium stearate | 0.5 |
| Weight at compression | 100.0 |

The active component is passed through a sieve with a mesh size of 250 μm and mixing is carried out with the lactose, the starch and the pregelatinized starch. The mixed powders are moistened with purified water, granulation is carried out, drying is carried out, sieving is carried out and mixing with magnesium stearate is carried out. The lubricated granules are compressed as in the direct compression formulae. A thin coating layer can also be applied to the tablets by means of appropriate film-forming materials, for example methylcellulose or hydroxypropylmethylcellulose, according to conventional techniques. The tablets can also be coated with sugar.

| Capsules | |
|---|---|
| | mg for one capsule |
| Active component | 10.0 |
| *Starch 1500 | 89.5 |
| Magnesium stearate, Codex | 0.5 |
| Filling weight | 100.0 |

*a form of directly compressible starch supplied by the firm Colorcon Ltd, Orpington, Kent, United Kingdom.

The active component is passed through a sieve with a mesh size of 250 μm and mixing with the other substances is carried out. The mixture is introduced into hard gelatin No. 2 capsules on a suitable filling machine. Other dosage units can be prepared by modifying the filling weight and, when necessary, by changing the size of the capsule.

| Syrup | |
|---|---|
| | mg per dose of 5 ml |
| Active component | 10.0 |
| Sucrose, Codex | 2750.0 |
| Glycerol, Codex | 500.0 |
| Buffer | |
| Flavor | |
| Colorant | q.s. |
| Preservative | |
| Distilled water | 5.0 |

The active component, the buffer, the flavor, the colorant and the preservative are dissolved in part of the water and the glycerol is added. The remainder of the water is heated to 80° C. and the sucrose is dissolved therein and the solution is then cooled. The two solutions are combined, the volume is adjusted and mixing is carried out. The syrup obtained is clarified by filtration.

| Suppositories | |
|---|---|
| Active component | 10.0 mg |
| *Witepsol H15 | remainder to 1.0 g |

*Tradename for Adeps Solidus from the European Pharmacopeia.

A suspension of the active component in Witepsol H15 is prepared and it is introduced into an appropriate machine with 1 g suppository molds. Liquid for administration by intravenous injection

| Liquid for administration by intravenous injection | |
|---|---|
| | g/l |
| Active component | 2.0 |
| Water for Injection, Codex | remainder to 1000.0 |

It is possible to add sodium chloride in order to adjust the tonicity of the solution and to adjust the pH to the maximum stability and/or in order to facilitate dissolution of the active component by means of a dilute alkali or acid or by adding appropriate buffer salts. The solution is prepared, is clarified and is introduced into phials of appropriate size which are sealed by melting the glass. It is also possible to sterilize the liquid for injection by heating in an autoclave according to one of the acceptable cycles. It is also possible to sterilize the solution by filtration and to introduce into a sterile phial under aseptic conditions. The solution can be introduced into the phials under a gaseous atmosphere.

| Cartridges for inhalation | |
|---|---|
| | g/cartridge |
| Micronized active component | 1.0 |
| Lactose, Codex | 39.0 |

The active component is micronized in a fluid-energy mill and converted to the form of fine particles before mixing with lactose for tablets in a high energy mixer. The pulverulent mixture is introduced into hard gelatin No. 3 capsules on an appropriate encapsulating machine. The contents of the cartridges are administered using a powder inhaler.

| Pressurized aerosol with a metering valve | | |
|---|---|---|
| | mg/dose | per 1 container |
| Micronized active component | 0.500 | 120 mg |
| Oleic acid, Codex | 0.050 | 12 mg |
| Trichlorofluoromethane for pharmaceutical use | 22.25 | 5.34 g |
| Dichlorodifluoromethane for pharmaceutical use | 60.90 | 14.62 g |

The active component is micronized in a fluid-energy mill and reduced to the form of fine particles. The oleic acid is mixed with the trochlorofluoromethane at a temperature of 10°–15° C. and the micronized medicament is introduced into the solution using a mixer with a high shearing effect. The suspension is introduced in a measured amount into aluminum aerosol containers to which are attached appropriate metering valves delivering a dose of 85 mg of the suspension; the dichlorodifluoromethane is introduced into the containers by injection through the valves.

We claim:

1. Compounds corresponding to the formula

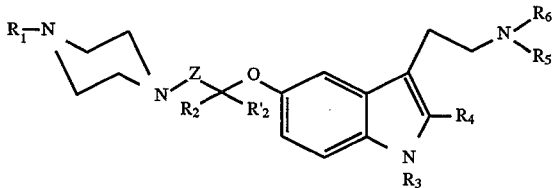

in which $R_1$ represents a hydrogen atom, a linear or branched $C_1$ to $C_6$ alkyl group or a phenyl, benzyl, $C_3$ to $C_7$ cycloalkyl, $C_7$ to $C_{12}$ polycycloalkyl, dibenzocycloalkyl, dibenzoxepine, dibenzoazepine, dibenzothiepine, benzopyrrolocycloalkyl, benzothienocycloalkyl or naphthyl group, optionally substituted by one or a number of substituents chosen from halogen atoms, the trifluoromethyl group, and $C_1$ to $C_6$ alkyl, aryl, acyl, alkoxy and alkylthio radicals, Z represents C=O, $SO_2$ or $(CH_2)_n$ in which n is between 0 and 5, $R_2$ represents a hydrogen atom, a linear or branched $C_1$ to $C_6$ alkyl group or a phenyl, benzyl, cycloalkyl, pyrrole, furan, pyridinyl or thioophenyl group, optionally substituted by one or a number of substituents chosen from halogen atoms and $C_1$ to $C_6$ alkyl, aryl, acyl, alkoxy and alkylthio groups, $R'_2$ represents a hydrogen atom, a linear or branched $C_1$ to $C_6$ alkyl group or a phenyl group, $R_3$ represents a hydrogen atom, a linear or branched $C_1$ to $C_6$ alkyl group or a benzyl or phenethyl group, $R_4$ represents a hydrogen, chlorine, fluorine, or bromine atom or a linear or branched $C_1$ to $C_6$ alkyl group, $R_5$ represents a hydrogen atom, a linear or branched $C_1$ to $C_6$ alkyl group or a benzyl or phenethyl group, $R_6$ represents a hydrogen atom, a linear or branched $C_1$ to $C_6$ alkyl group, $COR_7$, $CO_2R_7$, or $CONHR_7$, in which $R_7$ represents a linear or branched $C_1$ to $C_6$ alkyl group, or a variously substituted phenyl group, their salts, or solvates thereof.

2. A compound according to claim 1, wherein $R_1$ represents a phenyl group or a naphthyl optionally substituted by one or a number of substituents chosen from halogen atoms and $C_1$ to $C_6$ alkyl, aryl, acyl, alkoxy or alkylthio.

3. A compound according to claim 1, wherein $R_1$ represents a dibenzothiepine.

4. A compound according to claim 1, wherein Z represents CO.

5. A compound according to claim 1, wherein Z represents $SO_2$.

6. A compound according to claim 1, wherein Z represents $(CH_2)_n$ in which n is between 1 and 5.

7. A compound according to claim 1, wherein $R_2$ and $R'_2$ represent a hydrogen.

8. A compound according to claim 1, wherein $R_2$ represents a hydrogen.

9. A compound according to claim 1, wherein $R_2$ represents a methyl.

10. A compound according to claim 1, wherein $R_2$ represents a phenyl group optionally substituted by one or a number of substituents chosen from halogen atoms and alkyl, aryl, acyl, alkoxy or alkylthio groups.

11. A compound according to claim 1, wherein $R_3$ represents a hydrogen.

12. A compound according to claim 1, wherein $R_4$ represents a hydrogen.

13. A compound according to claim 1, wherein $R_5$ and $R_6$ represent a hydrogen.

14. A compound according to claim 1, wherein $R_5$ is a linear or branched alkyl group.

15. A compound according to claim 1, wherein $R_5$ and $R_6$ represent a linear or branched alkyl group.

16. A compound according to claim 1, in the form of a hydrochloride, hydrobromide, sulfate, fumarate or maleate salt.

17. A process for the preparation of the compound of claim 1 comprising reacting a compound of formula (II):

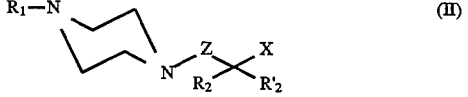

in which $R_1$, Z, $R_2$ and $R'_2$ have the meanings in claim 1 and where X is defined as a leaving group selected from the group consisting of a halogen where the halogen is selected from the group consisting of: bromine, iodine and chlorine, a mesylate, a tosylate and a triflate, with a compound of formula (III):

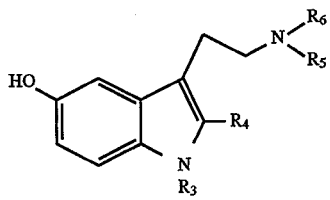
(III)

in which $R_3$, $R_4$, $R_5$ and $R_6$ having the meaning indicated in claim 1 and $R_6$ is other than a hydrogen atom.

18. A pharmaceutical composition comprising, as an active ingredient, a compound according to claim 1 in combination with an acceptable pharmaceutical vehicle.

19. A method of treating depression, anxiety, migraine, or vasospastic disorders, the method comprising administering to the patient an effective amount of at least one compound of claim 1.

* * * * *

UNITED STATES PATENT AND TRADEMARK OFFICE
CERTIFICATE OF CORRECTION

PATENT NO.    : 5,641,779
DATED         : June 24, 1997
INVENTOR(S)   : Serge Halazy et al.

It is certified that error appears in the above-identified patent and that said Letters Patent is hereby corrected as shown below:

Title Page,
Line 4, before "MEDICAMENTS", insert --AS--.

Column 1,
Line 4, before "MEDICAMENTS", insert --AS--;
Line 44, after "does" insert:
--not in any event either describe or suggest the piperazine derivatives described in the present invention.
The present invention relates to compounds of--.

Column 2,
Line 1, before "repesents" insert --$R_2$--.

Column 3,
Formula (II), first occurrence of "R'$_2$" should be 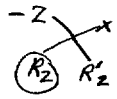
Line 61, "Byway" should be --By way--.

Column 4,
Line 64, "Group" should be --group--.

Column 5,
Line 5, "Group" should be --group--;
Line 11, "forma- tion" should be --formation--;
Line 27, "Group" should be --group--;
Line 30, "Generally" should be --generally--..

Column 6,
Line 61, after "an" delete the numeral --5--.

Column 7,
Line 27, "$K_2CO_3Cs_2CO_3$" should be --$K_2CO_3$, $Cs_2CO_3$--;
Line 41, "$BH_3.Me_3S$" should be --$BH_3 \cdot Me_2S$--

Column 13
Line 14, "a,a,a" should be --α,α,α--;
Line 28, "a,a,a" should be --α,α,α--.

UNITED STATES PATENT AND TRADEMARK OFFICE
CERTIFICATE OF CORRECTION

PATENT NO. : 5,641,779
DATED : June 24, 1997
INVENTOR(S) : Serge Halazy et al.

It is certified that error appears in the above-identified patent and that said Letters Patent is hereby corrected as shown below:

Column 14,
Line 1, "1-naphthylpiperazine" should be --1-naphthyl-piperazine--;
Line 4, "rag" should be --mg--, "retool" should be --mmol--.

Column 15,
Line 25, "retool" should be --mmol--;
Line 35, "$C_{29}H_{39}N_4Cl$" should be --$C_{29}H_{39}N_4O_4Cl$--.

Column 16,
Line 27, "$(C_{24}H_{32}Cl_2N_4O_2.1/3Et_2O)$" should be --$(C_{24}H_{32}Cl_2N_4O_2 \cdot 1/3Et_2O)$--.

Column 17,
Line 2, "rag" should be --mg--;
Line 4, "mag" should be --mg--;
Line 12 "$(C_{28}H_{37}Cl_2N_4O_5.1/4Et_2O)$" should be --$C_{28}H_{37}Cl_2N_4O_5 \cdot 1/4Et_2O$--;
Line 34, "d6" should be --$d_6$--.

Column 19,
Line 63, "d6" should be --$d_6$--.

Column 21,
Line 56, "1-naphthylpiperazine" should be --1-naphthyl-piperazine--.

Column 23,
Line 13, "rag" should be --mg--, "retool" should be --mmol--.
Line 63, "mmol" should be --mmol)--.

Column 25,
Line 36, after "%", insert --calculated--.

Column 26,
Line 45, "$C_{23}H_{30}N_4O_3Cl_2.1.7H_2$" should be --$C_{23}H_{30}N_4O_3Cl_2 \cdot 1.7H_2$--.

Column 27,
Line 26, "$C_{21}H_{32}N_4O_2Cl_2.0.7H_2O$" should be --$C_{21}H_{32}N_4O_2Cl_2 \cdot 0.7H_2O$--
Line 31, "S" should be --s--;
Line 37, "4-o-Tolyl)" should be --4-(o-Tolyl)--.

UNITED STATES PATENT AND TRADEMARK OFFICE
CERTIFICATE OF CORRECTION

PATENT NO.    : 5,641,779
DATED         : June 24, 1997
INVENTOR(S)   : Serge Halazy et al.

It is certified that error appears in the above-identified patent and that said Letters Patent is hereby corrected as shown below:

Column 28,
Line 10, delete "EXAMPLE 20";
Line 12, insert --20-- at the beginning of the line;
Line 27, "1from 1D", should be --1 from 1D--.

Column 30,
Line 60, before "5-HT$_{1A}$" insert --*--;
Line 65, before "5-HT$_{1c}$" insert --*--.

Column 31,
Line 16, "$^3$-idazoxan" should be --$^3$H-idazzoxan;
Line 17, "$^3$-RX821002" should be --$^3$H-RX821002--;

Column 34,
Lines 48-49, delete "Liquid for administration by intravenous injection".

Column 36,
Line 11, "COR,$_7$," should be --COR$_7$,--

Signed and Sealed this

Twenty first Day of August, 2001

*Attest:*

NICHOLAS P. GODICI
*Attesting Officer*        *Acting Director of the United States Patent and Trademark Office*